US006302898B1

(12) United States Patent
Edwards et al.

(10) Patent No.: US 6,302,898 B1
(45) Date of Patent: Oct. 16, 2001

(54) DEVICES FOR SEALING PUNCTURES IN BODY VESSELS

(75) Inventors: Stuart D. Edwards, Portola Valley; Thomas Wehman, Cupertino; Theodore L. Parker, Danville; Eugene V. Skalnyi, Mountain View; Theodore Kucklick, Los Gatos; John Evans, Fremont, all of CA (US)

(73) Assignee: Advanced Closure Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/021,708

(22) Filed: Feb. 10, 1998

Related U.S. Application Data

(63) Continuation-in-part of application No. 08/963,033, filed on Nov. 3, 1997, now abandoned, and application No. 08/963,082, filed on Nov. 3, 1997, and application No. 08/963,408, filed on Nov. 3, 1997, and a continuation-in-part of application No. 08/731,372, filed on Oct. 11, 1996, which is a continuation-in-part of application No. 08/319,373, filed on Oct. 6, 1994, which is a continuation-in-part of application No. 08/286,862, filed on Aug. 4, 1994, which is a continuation-in-part of application No. 08/272,162, filed on Jul. 7, 1994, which is a continuation-in-part of application No. 08/265,459, filed on Jun. 24, 1994.

(60) Provisional application No. 60/033,199, filed on Dec. 18, 1996.

(51) Int. Cl.$^7$ .................................................. A61B 17/08
(52) U.S. Cl. ................................................. 606/214; 606/213
(58) Field of Search ................................. 606/213, 215, 606/1, 192, 194, 198, 214; 604/96–103, 160, 161, 904, 51–53; 623/11; 600/23

(56) References Cited

U.S. PATENT DOCUMENTS

| 4,424,833 | 1/1984 | Spector et al. . |
| 4,555,242 | 11/1985 | Saudager . |
| 4,738,658 | 4/1988 | Magro et al. . |

(List continued on next page.)

FOREIGN PATENT DOCUMENTS

| 0 330 344 | 2/1988 | (EP) . |
| 0 476 178 A1 | 3/1992 | (EP) . |
| 0 482 350 A2 | 4/1992 | (EP) . |

(List continued on next page.)

OTHER PUBLICATIONS

Abergelm R. P., "Skin closure by Nd:YAG laser welding."*American Academy of Dermatology*. 1986 14(5):810–14.

Anand, R. K., et al. "Laser Balloon Angioplasty: Effect of Constant Temperature Versus Constant Power on Tissue Weld Strength." *Lasers in Surgery and Medicaine*. 1988. 8(1):40–44.

(List continued on next page.)

*Primary Examiner*—Gary Jackson
*Assistant Examiner*—Vikki Trinh
(74) *Attorney, Agent, or Firm*—Ryan Kromholz & Manion, S.C.

(57) ABSTRACT

A closure device is provided for sealing a puncture in a body vessel. The closure device includes an energy delivery device for delivering energy to tissue adjacent the vessel puncture which enhances an adhesiveness of the tissue to a closure composition precursor. The closure device includes a sealer/dilator for dilating tissue adjacent a vessel puncture, at least one closure composition precursor lumen within the sealer/dilator having an entrance port adjacent the proximal end of the sealer/dilator through which one or more fluent closure composition precursors can be delivered into the closure composition precursor lumen and an exit port adjacent the distal end of the sealer/dilator through which the one or more fluent closure composition precursors can be delivered outside the vessel adjacent the vessel puncture, and a plugging catheter for positioning within the vessel puncture, the plugging catheter extending distally from the sealer/dilator and including at least one position sensing mechanism such that the exit port of the closure composition precursor lumen is outside the vessel when the at least one position sensing mechanism is detected to be outside the vessel.

29 Claims, 25 Drawing Sheets

U.S. PATENT DOCUMENTS

| | | |
|---|---|---|
| 4,744,364 | 5/1988 | Kensey . |
| 4,838,280 | 6/1989 | Haaga . |
| 4,852,568 | 8/1989 | Kensey . |
| 4,874,368 | 10/1989 | Miller et al. . |
| 4,890,612 | 1/1990 | Kensey . |
| 4,891,359 | 1/1990 | Saferstein et al. . |
| 5,002,051 | 3/1991 | Dew et al. . |
| 5,021,059 | 6/1991 | Kensey et al. . |
| 5,041,129 | 8/1991 | Hayhurst et al. ..................... 606/232 |
| 5,042,985 | 8/1991 | Elliott et al. . |
| 5,053,046 | 10/1991 | Janese . |
| 5,057,106 * | 10/1991 | Kasevich et al. ...................... 606/33 |
| 5,061,274 | 10/1991 | Kensey . |
| 5,108,421 | 4/1992 | Fowler . |
| 5,129,882 | 7/1992 | Weldon et al. . |
| 5,156,613 | 10/1992 | Sawyer . |
| 5,159,937 | 11/1992 | Tremulis . |
| 5,163,906 | 11/1992 | Ahmadi . |
| 5,171,222 | 12/1992 | Euteneuer et al. . |
| 5,192,300 | 3/1993 | Fowler . |
| 5,197,971 | 3/1993 | Bonutti ............................... 606/192 |
| 5,221,259 | 6/1993 | Weldon et al. . |
| 5,222,974 | 6/1993 | Kensey et al. . |
| 5,250,025 | 10/1993 | Sosnowski et al. . |
| 5,275,616 | 1/1994 | Fowler . |
| 5,281,197 | 1/1994 | Arias et al. ............................ 604/57 |
| 5,282,827 | 2/1994 | Kensey et al. . |
| 5,290,310 | 3/1994 | Makower et al. ................... 606/213 |
| 5,292,309 | 3/1994 | Van Tassel et al. . |
| 5,292,332 | 3/1994 | Lee . |
| 5,306,254 | 4/1994 | Nash et al. . |
| 5,324,306 | 6/1994 | Makower et al. ................... 606/213 |
| 5,383,895 | 1/1995 | Gershony et al. . |
| 5,411,520 | 5/1995 | Nash et al. . |
| 5,413,571 | 5/1995 | Katsaros et al. . |
| 5,415,657 | 5/1995 | Taymor-Lurita . |
| 5,419,765 | 5/1995 | Weldon et al. ........................ 604/96 |
| 5,437,292 | 8/1995 | Kipshidze et al. ................... 128/898 |
| 5,441,517 | 8/1995 | Kensey et al. . |
| 5,447,502 | 9/1995 | Haaga ................................. 604/265 |
| 5,486,195 | 1/1996 | Myers et al. . |
| 5,496,332 | 3/1996 | Sierra et al. .......................... 606/139 |
| 5,507,744 | 4/1996 | Tay et al. . |
| 5,571,216 | 11/1996 | Anderson . |
| 5,575,815 | 11/1996 | Slepian et al. . |
| 5,591,204 | 1/1997 | Janzen et al. . |
| 5,591,205 | 1/1997 | Fowler . |
| 5,599,347 * | 2/1997 | Hart et al. ............................. 606/42 |
| 5,601,602 | 2/1997 | Fowler et al. . |
| 5,612,050 | 3/1997 | Rowe et al. . |
| 5,626,601 | 5/1997 | Gershony et al. . |
| 5,630,833 | 5/1997 | Katsoros et al. ..................... 606/213 |
| 5,649,959 | 7/1997 | Hannam et al. ..................... 606/213 |
| 5,653,730 | 8/1997 | Hammerslag ........................ 606/214 |
| 5,665,106 | 9/1997 | Hammerslag ........................ 606/214 |
| 5,665,107 | 9/1997 | Hammerslag ........................ 606/214 |
| 5,669,934 | 9/1997 | Sawyer ................................. 606/213 |
| 5,676,689 | 10/1997 | Kensey et al. . |
| 5,700,273 | 12/1997 | Buelna et al. ........................ 606/148 |
| 5,725,498 | 3/1998 | Janzen et al. .......................... 604/51 |
| 5,725,551 | 3/1998 | Myers et al. . |
| 5,728,132 | 3/1998 | Van Tassel et al. .................. 606/213 |

FOREIGN PATENT DOCUMENTS

| | | |
|---|---|---|
| 0 482 350 B1 | 12/1996 | (EP) . |
| 1 569 660 | 7/1977 | (GB) . |
| 91/09641 | 7/1991 | (WO) . |
| 92/22252 | 12/1992 | (WO) . |

OTHER PUBLICATIONS

Chuck, R. S., et al. "Dye–Enhanced Laser Tissue Welding." *Lasers in Surger and Medicine.* 1989. 9(5):471–477.

DeCoste, S. D., et al. "Dye–Enhanced Laser Welding for Skin Closure." *Lasers in Surgery and Medicine.* 1992. 12:25–32.

Fujitani, R. M., et al. "Biophysical Mechanisms of Argon Laser–Assisted Vascular Anastomoses." *Current Surgery.* Mar./Apr. 1998. pp. 119–123.

Goldstein, J. D., et al. "Development of a Reconstituted Collagen Tendon Proshesis." *The Journal of Bone and Joint Surgery.* 1989. 71–A(8):1183–91.

Grubbs, P. E., et al. "Enhanccement of $CO_2$ Laser Microvascular Anastomoses by Fibrin Glue." *Journal of Surgical Research.* 1988. 45:112–119.

Grubbs, P. E., et al. "Determinants of Weld Strength in Laser–Assisted Microvascular Anastomosis." *Current Surgery.* Jan–Feb. 1989. pp. 3–5.

Jain, K. K., et al. "Repair of small blood vessels with the Neodymium–YAG laser: A preliminary report." *Surgery.* 85(6):684–8.

Kopchok, G., et al. "Thermal Studies of In–Vivo Vascular Tissue Rusion by Argon Laser." *Journal of Investigative Surgery.* 1988. 1:5–12.

Kopchok, G., et al. "Argon laser vascular welding: he thermal component." *SPIE.* 1986. 712:260–3.

Kopchok, G. E., et al. "$CO_2$ and Argon Laser Veascular Welding: Acute Histologic and Thermodynamic Comparison." *Lasers in Surgery and Medicine.* 1988. 8:584–8.

Lemole, G. M., et al. "Preliminary evaluation of collagen as a componenet in the thermally–induced 'weld'." *SPIE.* 1991. 1422:116–22.

Mininberg, D. T., et al. "Laser welding of perdicled flap skin tubes." *The Journal of Urology.* 1989. 142(2):623–5.

Murray, L. W., et al. "Crosslinking of Extracellular Matrix Proteins." *Lasers in Surgery and Medicine.* 1989. 9:490–6.

Nimni, M. E. "Third International Congress of Biorhology Symposium on he Soft Tissues Around a Diarthrodial Joint." *Biorheology.* 1980. 17:51–82.

Oz, M. C., "Tissue soldering by use of indocyanine green dye–enhanced fibrinogen with the near infrared diode laser." *Journal of Vascular Surgery.* 1990. 11(5):718–25.

Oz, M. C., et al. "In Vitro Comparison of Thulium–Holmium–Chromiun–YAG and Argon lon Lasers. for Welding of Biliary Tissue." *Lasers in Surgery and Medicine.* 1989. 9:248–53.

Gilbert, P. T., et al. "Laser–Assisted Vasovasostomy."1989. 9:42–44.

Poppas, D. P., et al. "Laser Welding in Urethral Surgery: Improved Results with a Protein Solder." *The Journal of Urology.* 1988. 139:415–17.

Schober, R., et al. "Laser–Induced Alteration of Collagen Substructure Allows Microsurgical Tissue Welding." *Science.* Jun. 1986. 232:1421–2.

Tanzer, M. L., et al. "Cross–Linking of Collagen." *Science.* 180:561–6.

Vale, B. H., et al. "Microsurgical Anastomosis of Rat Carotid Arteries with the $CO_2$ Laser." *Plastic and Reconstructive Surgery.* 77(5):759–66.

White, R. A., et al. "Argon laser–welded arteriovenous anastomoses." *Journal of Vascular Surgery.* 1987. 6(5):447–53.

White, R. A., et al. "Comparison of Laser–Welded and Sutered Arteriotomies." *Arch Surg.* 1986. 121:1133–5.

White, R. A., et al. "Mechanism of Tissue Fusion in Argon Laser–Welded Vein–Artery Anastomoses." *Lasers in Surgery and Medicine.* 1988. 8:83–9.

* cited by examiner

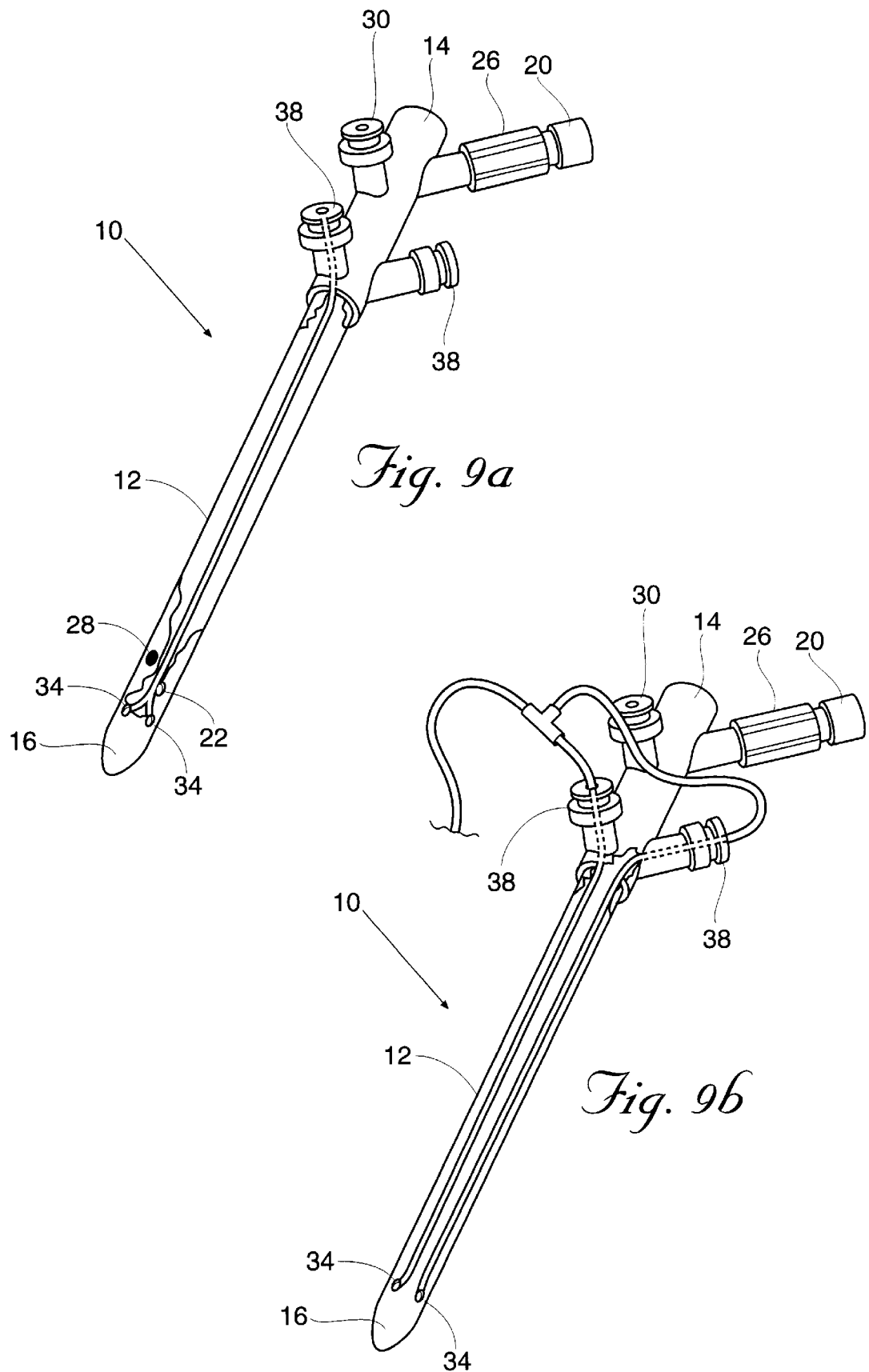

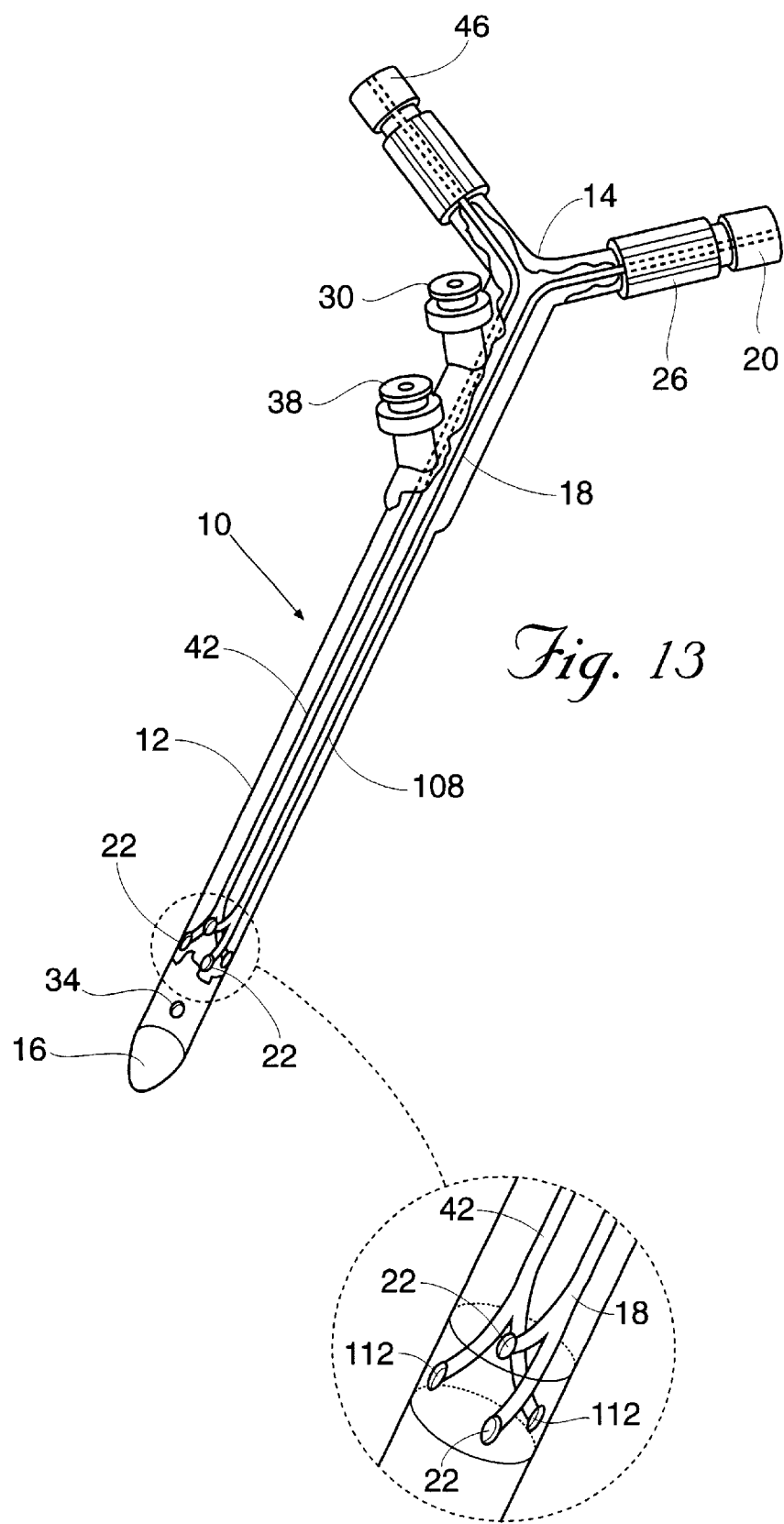

DEVICES FOR SEALING PUNCTURES IN BODY VESSELS

RELATIONSHIP TO COPENDING APPLICATION

This application is a continuation-in-part of Application Ser. No.: 08/963,033, Filed: Nov. 3, 1997, Entitled: Vascular Sealing Device; Application Ser. No.: 08/963,082, filed: Nov. 3, 1997, Entitled:In Situ Formed Non-fluent Closure Composition; and Application Ser. No.: 08/963,408, filed: Nov. 3, 1997, entitled: Vascular Sealing Device with Microwave Antenna which are each continuation-in-parts of Provisional U.S. Application Ser. No.: 60/033,199; Filed: Dec. 18, 1996, entitled "Universal Introducer", and a continuation-in-part of U.S. patent application Ser. No. 08/731,372 entitled "Thin Layer Ablation Apparatus" by Edwards et al. filed Oct. 11, 1996, which is a continuation-in-part of U.S. patent application Ser. No. 08/319,373 entitled "Thin Layer Ablation Apparatus" filed Oct. 6, 1994, which is a continuation-in-part of U.S. Application Ser. No. 08/286,862 entitled "Thin Layer Ablation Apparatus" by Edwards, et al, filed Aug. 4, 1994, which is a continuation-in-part of U.S. patent application Ser. No. 08/272,162 entitled "Thin Layer Ablation Apparatus" by Edwards, et al, filed Jul. 7, 1994, which is a continuation-in-part of U.S. patent application Ser. No. 08/265,459 entitled "Thin Layer Ablation Apparatus" by Edwards, filed Jun. 24, 1994, all of which are incorporated by reference.

FIELD OF THE INVENTION

This invention relates to a vessel closure device, and more particularly to a device for effecting the closure of a vessel by delivering a fluent closure composition precursor and converting the composition in situ to a non-fluent closure composition.

BACKGROUND OF THE INVENTION

A wide variety of surgical procedures are performed by the introduction of a catheter into a vessel. After the surgical procedure is completed, closure of the vessel at the site where the catheter was introduced is needed. Vessel punctures formed in the process of performing a catheter based surgical procedure are commonly 1.5 mm to 7.0 mm in diameter and can be larger. Closure of these punctures is frequently complicated by anticoagulation medicine given to the patient which interferes with the body's natural clotting abilities.

Closure of a vessel puncture has traditionally been performed by applying pressure to the vessel adjacent the puncture site. This procedure requires the continuous attention of at least one medical staff member to apply pressure to the vessel puncture site and can take as long as 30 minutes.

Devices have been developed for effecting the closure of vessel punctures through the application of energy. See U.S. Pat. Nos. 5,626,601; 5,507,744; 5,415,657; and 5,002,051. Devices have also been developed for effecting the closure of vessel punctures through the delivery of a mechanical mechanism which mechanically seals the puncture. See U.S. Pat. Nos.: 5,441,520; 5,441,517; 5,306,254; 5,282,827; and 5,222,974. Devices have also been developed for effecting the closure of vessel punctures through the delivery of a composition to block the vessel puncture. See U.S. Pat. Nos.5,601,602; 5,591,205; 5,441,517; 5,292,332; 5,275,616; 5,192,300; and 5,156,613. Despite the various devices that have been developed for closing vessel punctures, a need still exists for a simple, safe and inexpensive device and method for closing vessel punctures.

SUMMARY OF THE INVENTION

The present invention relates to a device and method for sealing a puncture in a body vessel. In one embodiment, the device has an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; and at least one position sensing mechanism positioned distal relative to the exit port such that the exit port is outside the vessel when the at least one position sensing mechanism is detected to be outside the vessel.

The closure device of this embodiment may optionally further include an energy delivery device for delivering energy adjacent the distal end of the elongated body to the fluent closure compound precursor. In one variation, the device includes a microwave antenna for delivering microwave energy adjacent the distal end of the elongated body to the fluent closure compound precursor. In another variation, the device includes a waveguide for delivering light energy adjacent the distal end of the elongated body to the fluent closure compound precursor. In yet another variation, the device includes a RF electrode for delivering RF energy adjacent the distal end of the elongated body to the fluent closure compound precursor.

In another embodiment, the device includes an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; and a microwave antenna for delivering microwave energy adjacent the distal end of the elongated body to the fluent closure compound precursor. The microwave antenna according to this embodiment is preferably incorporated onto the elongated body adjacent the body distal end.

In another embodiment, the device includes an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; a guidewire lumen within the elongated body; and a guidewire including microwave antenna for delivering microwave energy adjacent the distal end of the elongated body to the fluent closure compound precursor.

The present invention also relates to a method for sealing a puncture in a body vessel. In one embodiment, the method includes the steps of delivering a distal end of an elongated body into a lumen of the body vessel, the elongated body having at least one closure composition precursor lumen with a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture, and at least one position sensing mechanism positioned distal relative to the exit port such that the exit port is outside the vessel when the at least one position sensing mechanism is detected to be outside the vessel; withdrawing the elongated body until the at least one position sensing mechanism is positioned outside the vessel lumen; delivering one or more fluent closure composition precursors outside the vessel adjacent the vessel puncture; and transforming the one or more fluent closure composition precursors into a non-fluent closure composition which seals the vessel puncture.

In one variation, the method further includes the step of delivering energy adjacent the distal end of the elongated body to the fluent closure compound precursor to transform the one or more fluent closure composition precursors into the non-fluent closure composition. The energy may be microwave energy and the at least one of the one or more fluent closure composition precursors may optionally include a microwave energy absorbing material.

The present invention also relates to a non-fluent closure composition for closing a puncture in a vessel. In one embodiment, the non-fluent closure composition is formed by delivering a fluent closure composition precursor to a position outside the vessel adjacent to the puncture; and transforming the fluent closure composition precursor in situ to a non-fluent closure composition. In another embodiment, the non-fluent closure composition is formed by delivering two or more fluent closure composition precursors to a position outside the vessel adjacent to the puncture; and mixing the two or more fluent closure composition precursors to form a non-fluent closure composition in situ adjacent the vessel puncture.

Transforming the fluent closure composition precursor in situ may include solidifying the closure composition precursor or causing the closure composition precursor to chemically react with itself to form a non-fluent composition, the chemical reaction optionally being catalyzed by a catalyst or by energy. Energy used in the method may be any form of energy including, for example, RF energy and microwave energy. When microwave energy is used, the closure composition precursor includes a microwave energy absorbing material.

The present invention also relates to a method for improving the adhesiveness of tissue surfaces to sealants and adhesives by applying energy to a surface of tissue to which a sealant or adhesive is to be applied. The energy thermally modifies the tissue surface and causes the tissue to be more adherent to sealants and adhesives, such as closure composition used in the present invention. The thermal modification preferably includes blanching the tissue surface. The thermal modification is believed to reduce the water content at the tissue surface, remove materials at the tissue surface which interfere with the adhesiveness of tissue surfaces to sealants and adhesives, change the topography at the tissue surface, and preferably increase the surface area at the tissue surface, all of which serve to increase the tissue surface's ability to adhere sealants and adhesives. Thermal modification of the tissue surface may be performed with any suitable form of energy, including for example, electromagnetic energy (RF energy, light, and microwave energy), ultrasound, and other thermal heat sources.

The present invention also relates to a method for improving the adhesiveness of tissue surfaces to sealants and adhesives by applying a chemical agent to a surface of tissue to which a sealant or adhesive is to be applied. The chemical agent modifies the tissue surface such that the tissue surface is more adherent to sealants and adhesives, such as closure composition used in the present invention. The chemical modification preferably includes denaturing the tissue surface.

In one variation, basic chemical agents (i.e., having a pH greater than 7) capable of modifying a tissue surface are used. Examples suitable basic chemical agents include but are not limited to aqueous sodium bicarbonate, aqueous sodium carbonate, water solutions or suspensions of alkali or alkali earth oxides and hydroxides, aqueous ammonia, water soluble amines such as alkanol amines, basic amino acids such as lysine and poly(lysine), aqueous sodium lysinate, and basic proteins such as albumin.

In another variation, acidic chemical agents (i.e., having a pH less than 7) having an osmolality above that of blood are used which are capable of modifying a tissue surface.

In yet another variation, a chemical agent which can serve as a tissue etchant is used. Examples of suitable tissue etchants include, but are not limited to salicyclic acid, carboxylic acids, α-hydroxy carboxylic acids, and peroxides.

BRIEF DESCRIPTION OF THE DRAWINGS

FIG. 9A illustrates a closure device with a plurality of pressure ports coupled to a single position lumen.

FIG. 9B illustrates a closure device with a plurality of pressure ports coupled to the same tubing before the tubing is coupled to the pressure sensor.

FIG. 13 is a cross section of a closure device which alternate the precursor exit ports from a first closure compound with the precursor exit ports of a second closure compound.

FIG. 19A illustrates positioning the plugging catheter within the vessel.

FIG. 19B illustrates applying pretreatment energy to the vessel and to tissue adjacent the vessel.

FIG. 19C illustrates positioning the closure device so that the position sensor is located outside the vessel.

FIG. 19D illustrates delivering the closure composition precursor adjacent the vessel puncture.

DETAILED DESCRIPTION OF THE PREFERRED EMBODIMENT

Figure 1A:
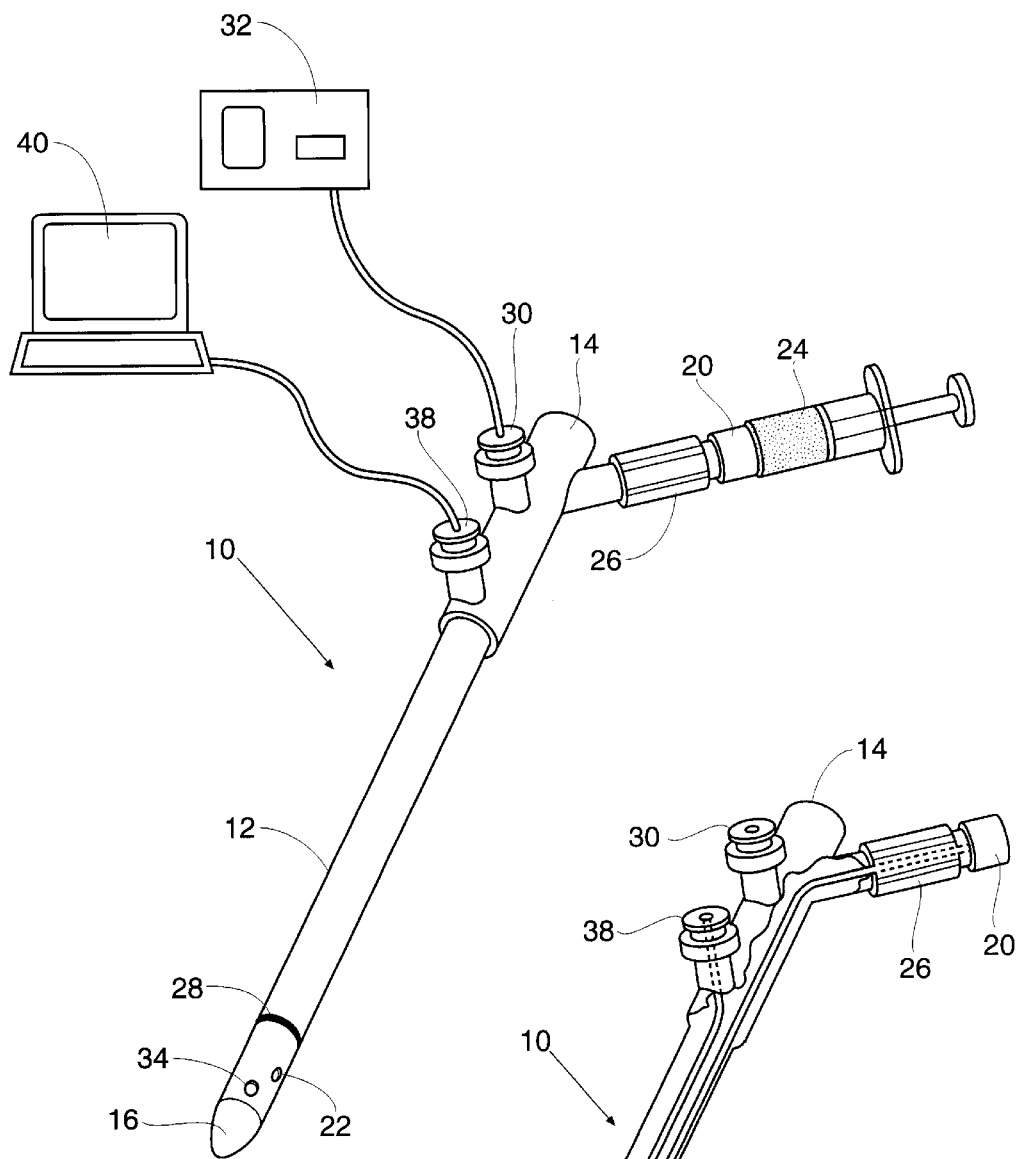
FIG. 1A is a sideview of a closure device according to the present invention.
Figure 1B:
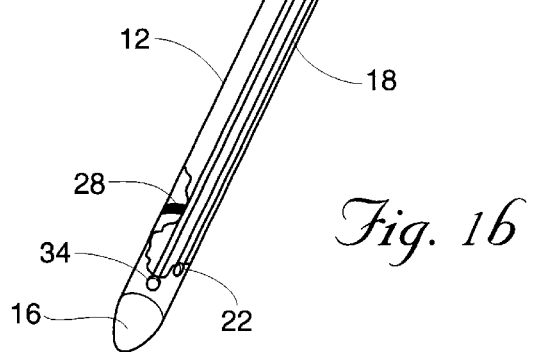
FIG. 1B is a cross section of the closure device of FIG. 1A.

FIGS. 1A and 1B illustrate a closure device 10 according to the present invention. The closure device 10 may be used to seal a puncture in a vessel such as a femoral artery.

The closure device 10 includes an elongated body 12 with a proximal end 14 and a distal end 16 sized to be inserted into a lumen of a vessel. The surface of the elongated body 12 is preferably made of a non-stick material, such as TEFLON, or coated with a biocompatible lubricant. Positioned within the elongated body 12 are one or more closure lumens which extend from adjacent the proximal end 14 of the device to the distal end 16 of the device for introducing a closure composition precursor adjacent the vessel puncture site. Illustrated in FIGS. 1A and 1B is a closure device 10 with a single closure lumen 18 with a precursor entrance port 20 and at least one precursor exit port 22 adjacent the distal end 16. The precursor entrance port 20 is preferably removably coupleable to a closure composition precursor source 24 for supplying the closure composition precursor to the closure device 10. The closure lumen 18 may optionally contain an anti-backflow valve 26 to prevent blood from flowing into the closure lumen 18 from the vessel.

The closure composition precursor can be formed of one or more fluent materials that can be flowed from the closure composition precursor source 24 to adjacent the device distal end 16 through the closure lumen 18. The fluent closure composition precursor is transformed into a non-fluent closure composition in situ to effect closure of the puncture. In a preferred embodiment, energy is applied to the closure composition precursor to accelerate its transformation into the non-fluent closure composition. The transformation of the fluent precursor to a non-fluent closure composition may be the result of a phase change (i.e. solidification) of the precursor or a chemical modification of the precursor. For example, the precursor may be formed from multiple components which react with each other, optionally accelerated by a catalyst or energy. Alternatively, the precursor may be formed from a single component which reacts with itself, also optionally accelerated by a catalyst or energy.

In embodiments where energy is applied, the body 12 includes an energy delivery device 28 adjacent the distal end 16. The energy delivery device 28 may be designed to deliver one or more different types of energy including but not limited to electromagnetic radiation (RF, microwave, ultraviolet, visible light, laser), ultrasound, resistive heating, exothermic chemical heating, and frictional heating. The energy source may also function to withdraw energy, i.e., perform cooling. The closure device 10 may also include an energy source attachment mechanism 30 for placing the energy delivery device 28 in energetic communication with an energy source 32.

The body 12 further includes at least one position sensing mechanism 34 adjacent the distal end 16 of the closure device 10 for indicating whether the position sensing mechanism 34 is located within or outside of the vessel 36. The position sensing mechanism 34 should be positioned on the body 12 distal to the precursor exit port 22 so that when the position sensing mechanism 34 is outside the vessel 36 the precursor exit port 22 is also outside the vessel 36. FIG. 1A illustrates the closure device 10 with a single position sensing mechanism 34. As illustrated, the closure device 10 may also include a position monitor attachment port 38 for coupling the position sensing mechanism 34 to a position monitor 40. Examples of a position sensing mechanisms include, but are not limited to, a pressure port and an electrical contact switch.

Other sensors (not shown) may also be positioned on the body 12. For instance, a temperature sensor for measuring temperature adjacent the distal end 16 of the body 12 and/or an impedance sensor may be positioned at the distal end 16 of the closure device 10.

Figure 2:
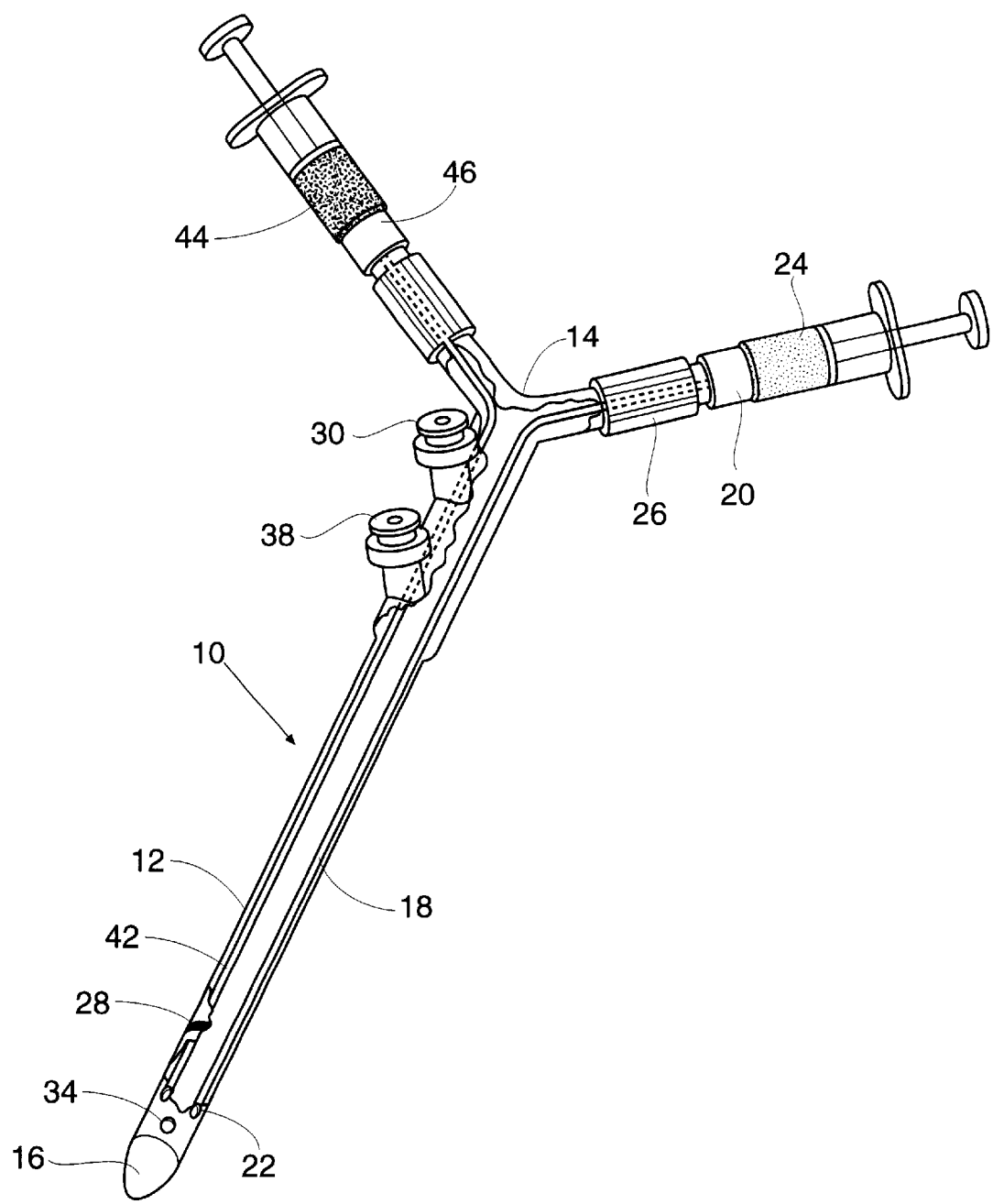
FIG. 2 is a cross section of a closure device with a first and second closure lumen coupled to first and second closure composition precursor sources.

The body 12 can include two or more closure lumens for the introduction of closure composition precursor. For example, as illustrated in FIG. 2, a second closure lumen 42 may be coupled to a second closure composition precursor source 44 by a second precursor entrance port 46. The second closure lumen 42 may also contain an anti-backflow valve 26 to prevent blood flow through the second closure lumen 42.

The closure composition precursor may be introduced adjacent the vessel puncture as a single composition through a single closure lumen. Alternately, a first composition may be introduced through the closure lumen 18 and a second composition can be introduced through the second closure lumen 42, as illustrated in FIG. 2. The first and second compositions can be the same or different and can be introduced simultaneously or at different times. The first and second compositions may interact to accelerate the transformation to the non-fluent closure composition at the tissue site 54, for example, by reacting with each other or by one catalyzing the solidification of the other.

Figure 3A:
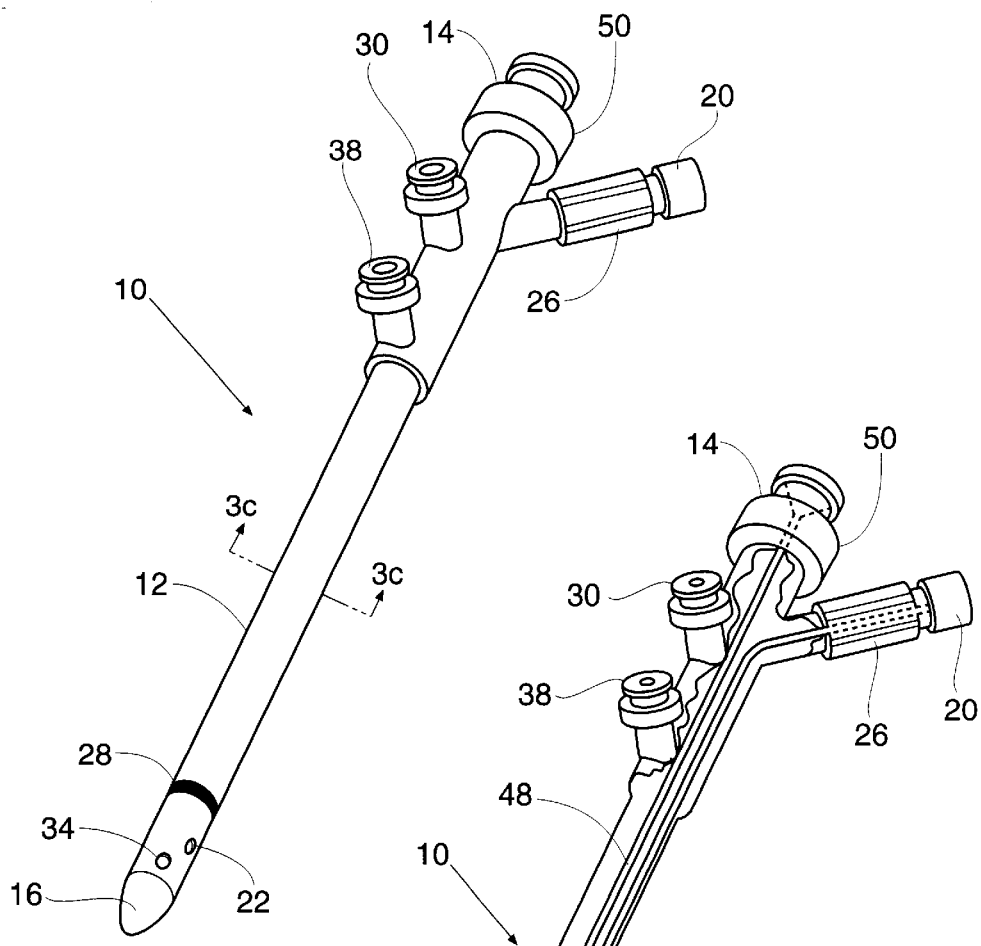
FIG. 3A is a sideview of a closure device including a guidewire lumen configured to accommodate a guidewire.
Figure 3B:
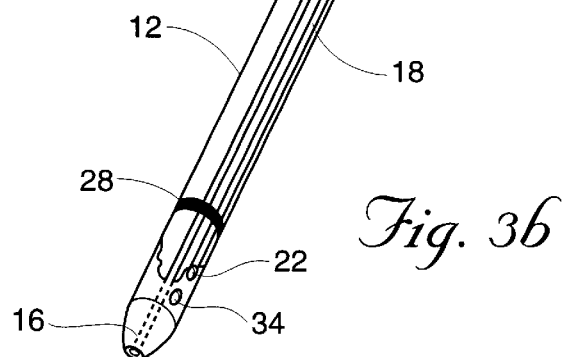
FIG. 3B is a cross section of a closure device illustrated in FIG. 3A.
Figure 3C:
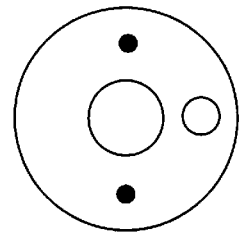

FIGS. 3A–3B illustrate another embodiment of the invention configured to be used with a guidewire. As illustrated in FIG. 3A, the body 12 can include a guidewire lumen 48 configured to accommodate a guidewire. The guidewire lumen 48 can include an anti-backflow valve or hemostasis valve 50. FIG. 3B illustrates a cross-section of the device illustrated in FIG. 3B.

Figure 4A:
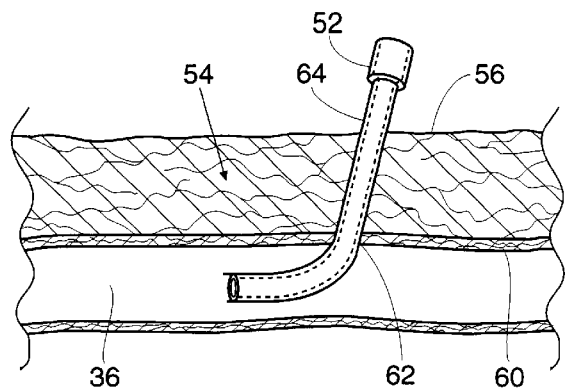
FIG. 4A illustrates a sheath with a distal end disposed within a vessel.

FIGS. 4A–4F illustrate a method of using the closure device 10 illustrated in FIGS. 1A–1B. The closure device 10 is used after a surgical procedure where a vessel 36 such as a femoral artery has been punctured. Angioplasty is a typical surgery which results in puncturing the femoral artery with a catheter. After the catheter devices from such a surgical procedure have been removed, a sheath 52 typically remains within a tissue site 54 as illustrated in FIG. 4A. The sheath 52 penetrates the skin 56 of the patient and passes through the underlying tissue to a vessel 60. The distal end 16 of the sheath 52 is positioned through a puncture 62 in the vessel 60.

Figure 4B:
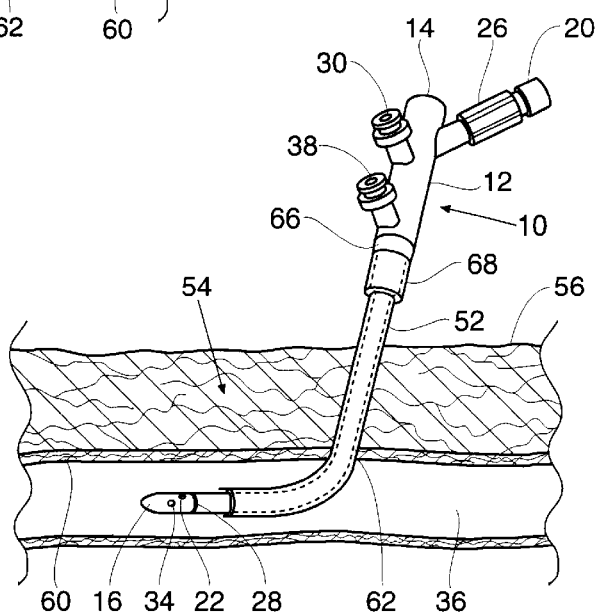
FIG. 4B illustrates a closure device disposed within the sheath such that the distal end of the closure device extends beyond the distal end of the sheath.

As illustrated in FIG. 4B, the closure device 10 is inser into the sheath lumen 64. The position of the closure device 10 within the sheath 52 may be set by fixing the closure device 10 to the sheath. For example, as illustrated, the closure device 10 may include a stop collar 66 which may engage an upper flange 68 on the sheath 64. The distal end 16 of the closure device 10 extends from the sheath 52 such that the position sensor 30 and precursor exit port 22 are distal relative to the sheath 52 and positioned within the vessel 60.

Figure 4C:
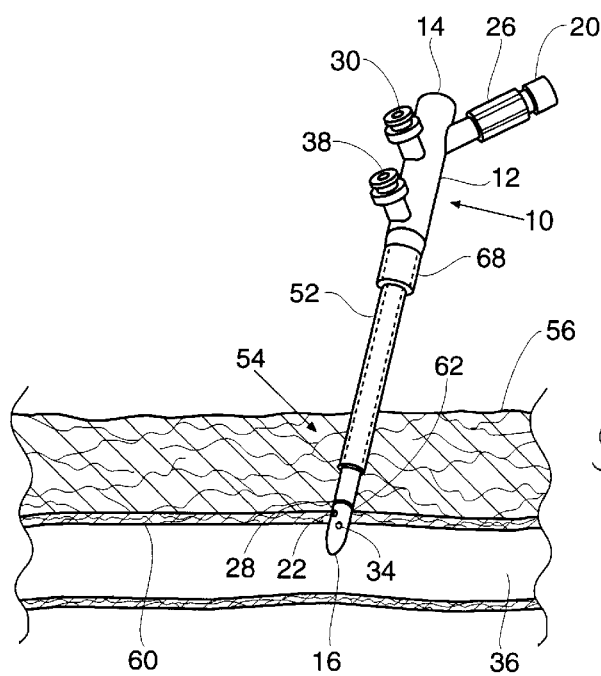
FIG. 4C illustrates the sheath and closure device withdrawn from the vessel until the position sensing mechanism is located outside the vessel adjacent the puncture.

As illustrated in FIG. 4C, the sheath 52 and closure device 10 are simultaneously withdrawn until the position sensor 30 is sensed to be located outside the vessel 60. Since the precursor exit port 22 is positioned distal relative to the position sensor 30, the precursor exit port 22 is necessarily positioned outside the vessel 60 when the position sensor is outside the vessel 60.

Figure 4D:
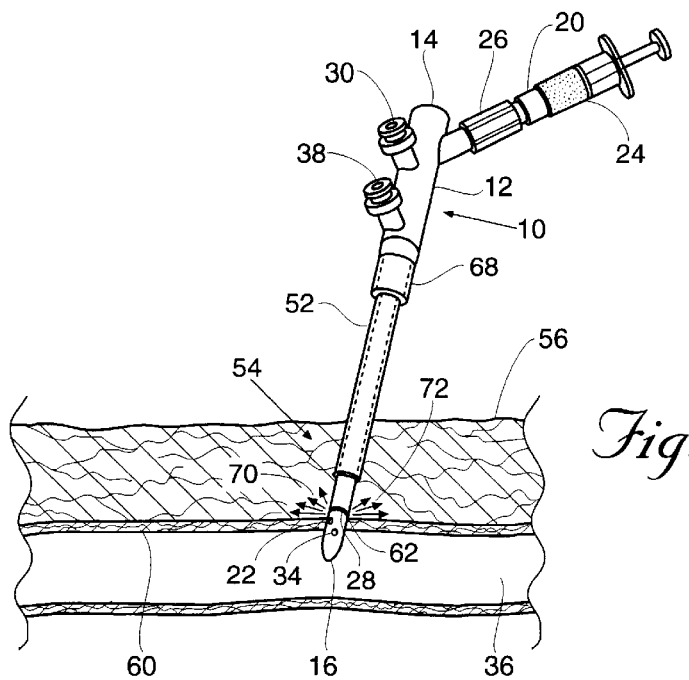
FIG. 4D illustrates a closure composition precursor source coupled to the closure device of FIG. 4C. The closure composition precursor is delivered through the closure lumen to the puncture.

As illustrated in FIG. 4D, a fluent closure composition precursor 70 is delivered through the closure lumen 18 and out the precursor exit port 22 after the precursor exit port 22 is determined to be outside the vessel 60. The fluent closure composition precursor 44 should have sufficiently low viscosity to allow the closure composition precursor to flow through the closure lumen 18. Once delivered, the closure composition precursor 44 accumulates adjacent the vessel 60. The transformation of the closure composition precursor to a non-fluent closure composition serves to seal the vessel puncture 62. Energy can optionally be delivered from the energy delivery device 28 to the closure composition precursor as illustrated by arrows 72 in order to cause and/or accelerate transformation to the non-fluent closure composition. Alternatively or in addition, a catalyst can be added to catalyze the conversion of the fluent precursor to a non-fluent closure composition.

Figure 4E:
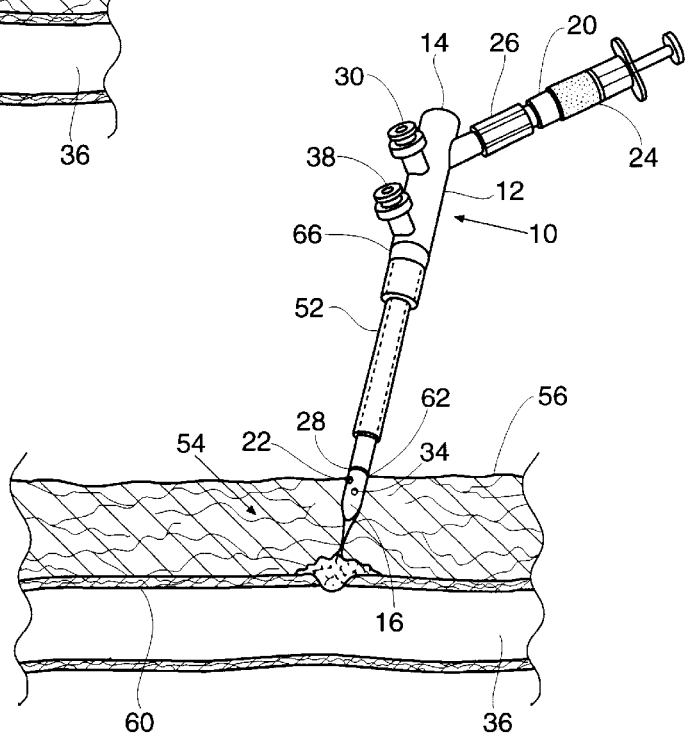
FIG. 4E illustrates the puncture after the closure device of FIG. 4D is withdrawn from the puncture.

FIG. 4E illustrates the withdrawal of the closure device 10.

Figure 4F:
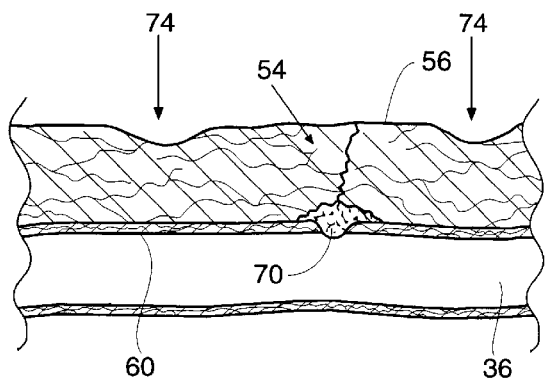
FIG. 4F illustrates the puncture after the closure device is completely withdrawn from the tissue site.

In FIG. 4F the closure device 10 is completely withdrawn from the tissue site 54 and pressure is being applied at the arrows 74 for a sufficient period of time after the closure composition precursor is delivered to allow the closure composition to transition to non-fluent closure composition.

Figure 5A:
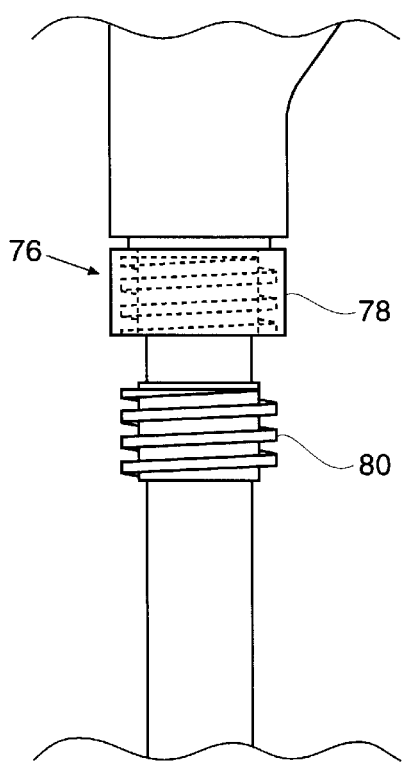
FIG. 5A is a sideview of a locking mechanism coupled to a closure device and threads on a sheath.
Figure 5B:
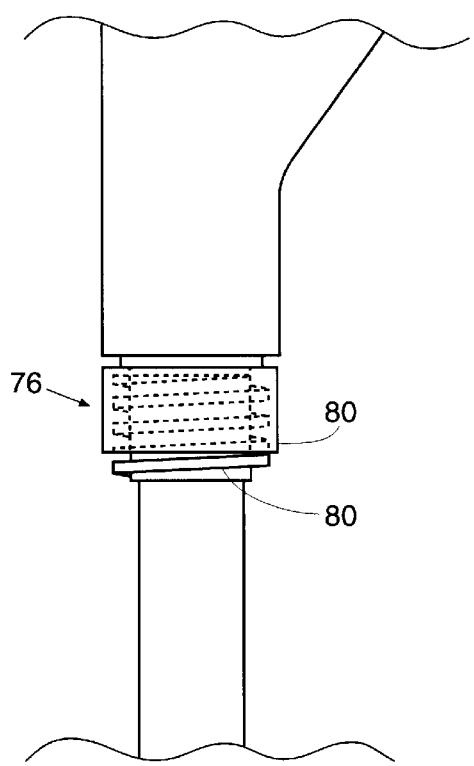
FIG. 5B is a sideview of the locking mechanism of FIG. 5A coupled to the threads on a sheath.

The body 12 can optionally further include a locking mechanism 76 for coupling the closure device 10 to the sheath 52. For example, as illustrated in FIGS. 5A and 5B, the locking mechanism 76 can be a threaded nut 78 complementary to threads 80 at the proximal end 14 of the sheath 52. When the closure device 10 is positioned within the sheath 52 the threaded nut 78 is turned to engage the threads 80 on the sheath 52 as illustrated in FIG. 5B. As a result, the sheath 52 and closure device 10 move as a unitary body. Movement as a unitary body is desirable to prevent the closure device 10 from moving relative to the sheath 52 when the closure device 10 is withdrawn from the tissue site 54. Other mechanisms can be used to lock the closure device to a sheath including, for example, straps, snap-fit arrangements, bayonet locks, magnets, adhesives, and detents.

Figure 6A:
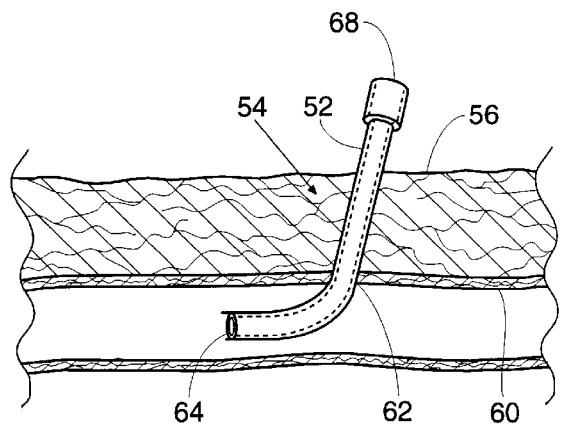
FIG. 6A illustrates a sheath with a distal end disposed within a vessel.

FIGS. 6A–6G illustrate a method of using the closure device 10 illustrated in FIGS. 3A–3B which include a guidewire. As discussed with regard to the method illustrated by FIGS. 4A–4F, the method makes use of a sheath 52 left in place after a surgical procedure. FIG. 6A illustrates the sheath 52 in place in a tissue site 54 after the surgical procedure.

Figure 6B:
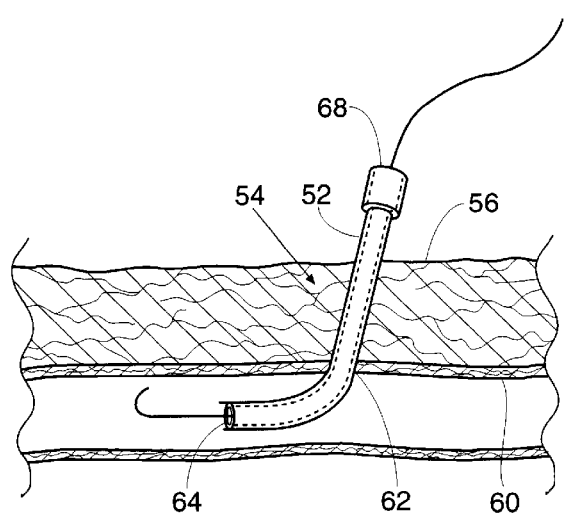
FIG. 6B illustrates a guidewire disposed within the sheath of FIG. 6A.

As illustrated in FIG. 6B a guidewire 82 is inserted into the vessel 60 through the sheath lumen 64.

Figure 6C:
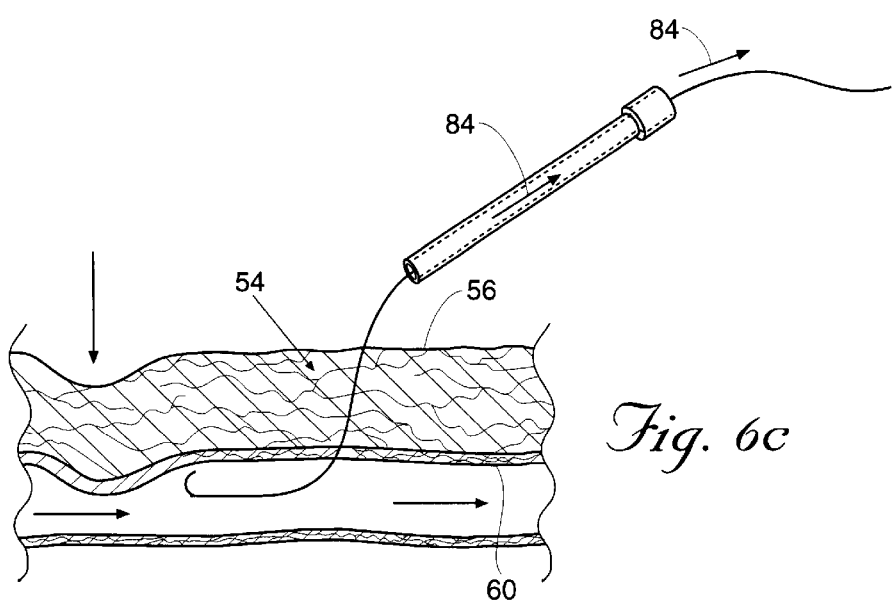
FIG. 6C illustrates the sheath of FIG. 6B withdrawn along the guidewire.

Pressure is applied to the skin 56 upstream from the puncture 62 as shown by arrow 76 in FIG. 6C to prevent bloodflow through the vessel 60. The sheath 52 is then withdrawn from the tissue site 54 along the guidewire 82 as illustrated by arrow 84.

Figure 6D:
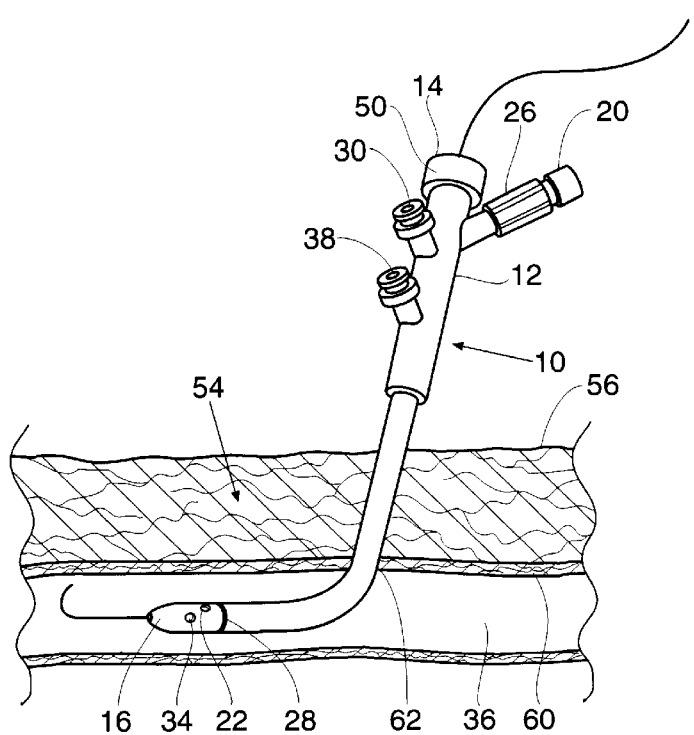
FIG. 6D illustrates a closure device threaded along the guidewire of FIG. 6C until the distal end of the device is disposed within a vessel.

As illustrated in FIG. 6D, the guidewire 82 is then thread within the guidewire lumen 48 of the closure device 10 and the distal end 16 is pushed forward through the tissue site 54 until the position sensor 30 indicates that the position sensor 30 is within the vessel 60. The distal end 16 of the closure device 10 preferably has the same or larger diameter as the sheath used in the surgical procedure. Since the puncture 62 has been dilated to the diameter of the sheath 52, this sizing reduces leakage of blood between the puncture 62 and the closure device 10.

Figure 6E:
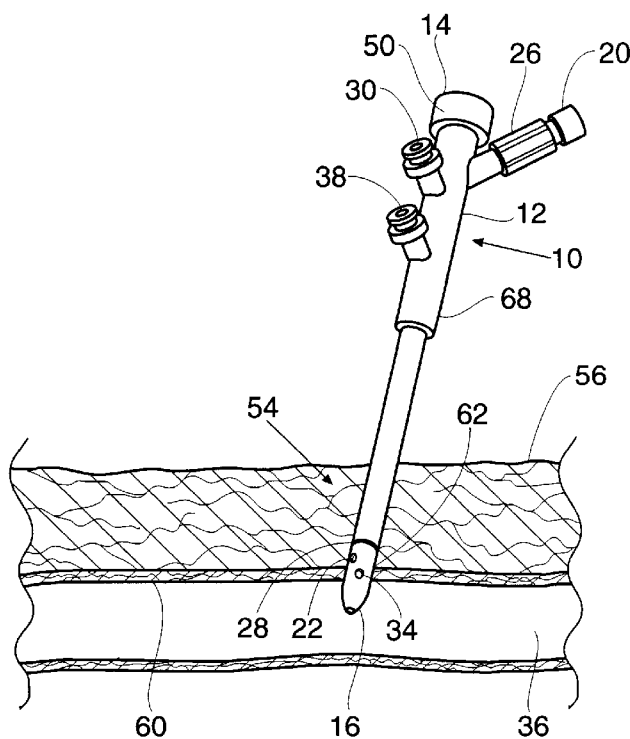
FIG. 6E illustrates the closure device of FIG. 6D after the guidewire has been withdrawn. The closure device is withdrawn until the position sensing mechanism is located outside the vessel adjacent the puncture.

As illustrated in FIG. 6E, the closure device 10 is slowly withdrawn from the vessel 60 until the position sensor 30 indicates that the position sensor 30 is located outside the vessel 60. Since the precursor exit port 22 is positioned proximally relative to the position sensor 30, withdrawal of the position sensor from the vessel 60 assures that the precursor exit port 22 has been withdrawn from the vessel 60.

Figure 6F:
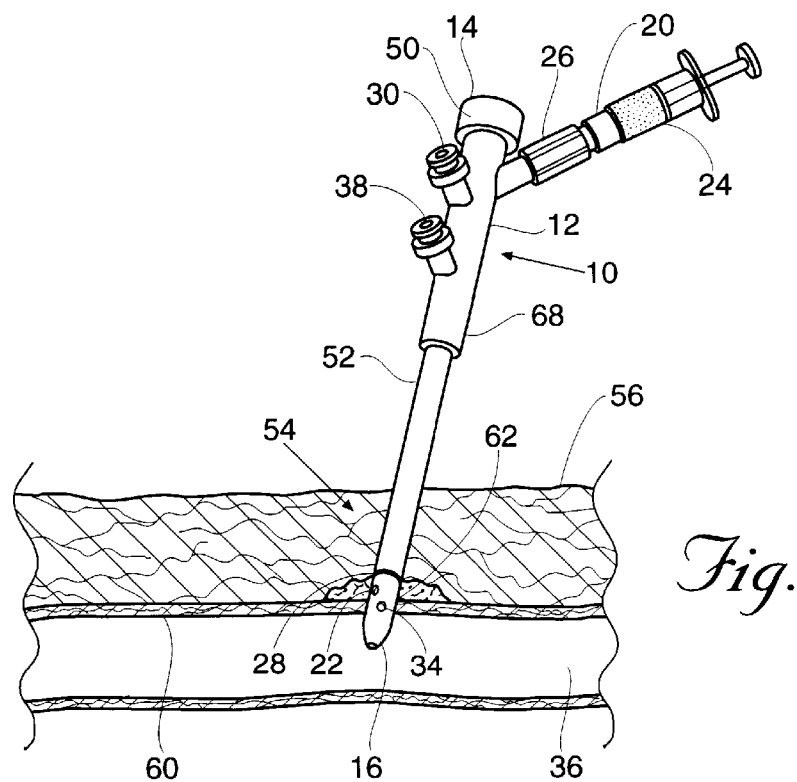
FIG. 6F illustrates a closure composition precursor source coupled to the closure device of FIG. 6E. The closure composition precursor is delivered through the closure lumen to the puncture.

As illustrated in FIG. 6F, once the precursor exit port 22 is determined to be outside the vessel 60, a closure composition precursor 44 is delivered through the closure lumen 18 and out the precursor exit port 22 adjacent the vessel puncture 62.

Figure 6G:
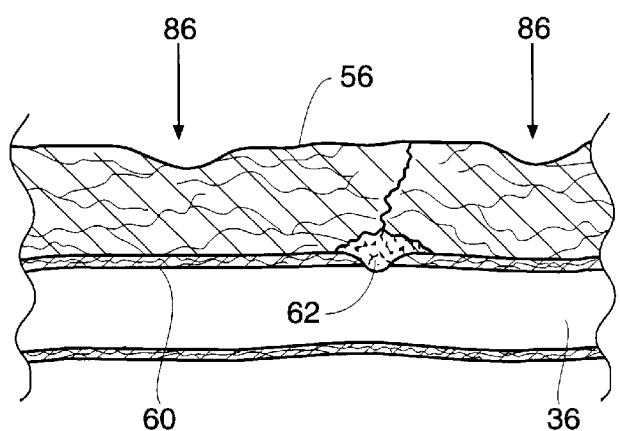
FIG. 6G illustrates the puncture after the closure device is completely withdrawn from the tissue site.

FIG. 6G illustrates the complete withdrawal of the closure device 10 from the tissue site 54. Pressure is applied at the arrows 86 until desired transformation of the fluent closure composition precursor to the non-fluent closure composition is substantially completed.

The energy delivery device 28 can be optionally used to deliver a form of energy which functions to accelerate the transformation of the fluent closure composition precursor to non-fluent closure composition. Alternatively or in addition, a catalyst can be added to catalyze the conversion of the fluent precursor to a non-fluent closure composition. Most commonly, energy is used to increase the temperature of the closure composition precursor. In one embodiment, the energy delivery device 28 is a microwave antenna positioned on or within the body 12. The guidewire 82 can also include a microwave antenna. When microwave energy is employed, the closure composition precursor preferably includes materials capable of absorbing microwave energy. Examples of such materials include, but are not limited to, hematite ($\alpha$-$Fe_2O_3$), maghemite (y-$Fe_2O_3$), magnetite ($Fe_3O_4$), geothite ($\alpha$-FeOOH), lepidocrocite (y-FeOOH), ferrihydrite, feroxyhyte ($\delta$-FeOOH), akageneite ($\beta$-FeOOH) graphite and amorphous carbon.

Figure 7A:
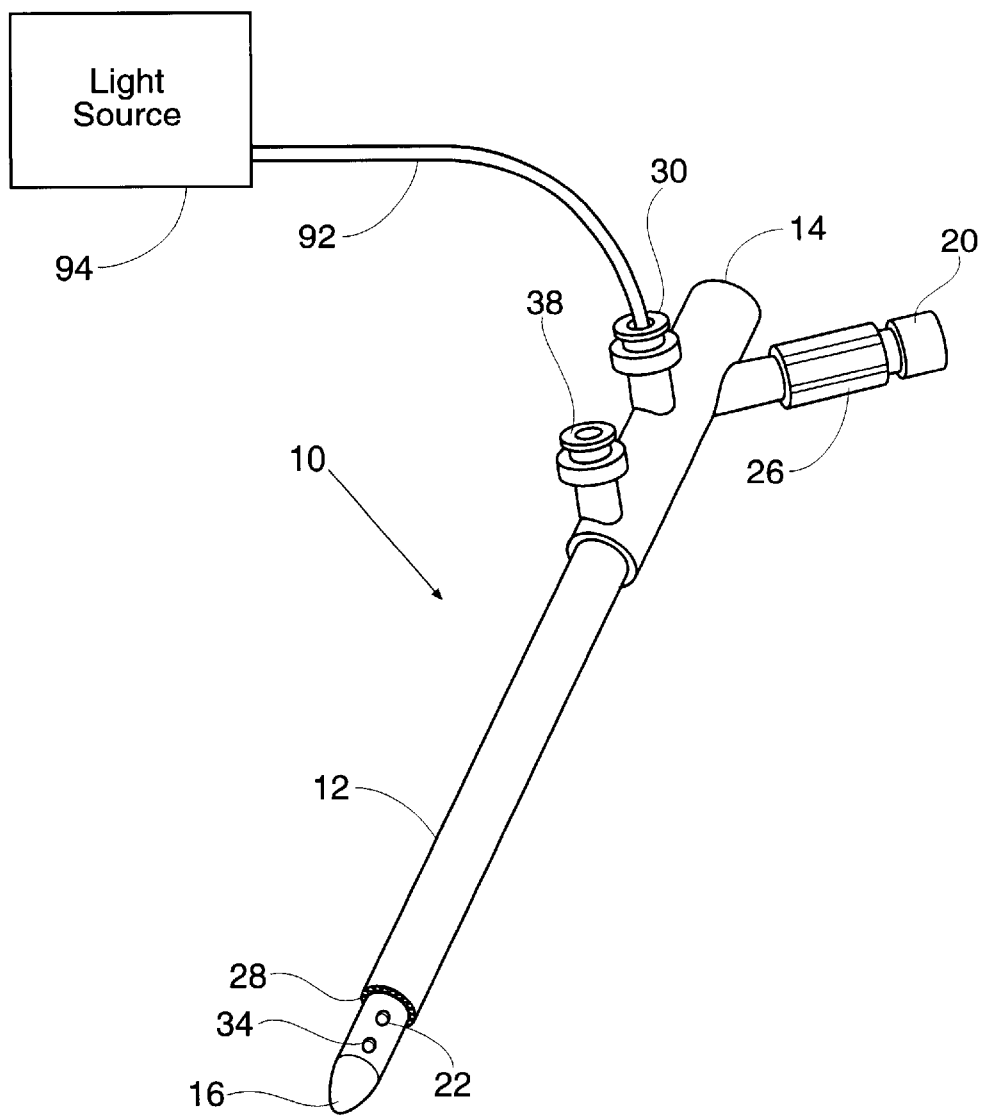
FIG. 7A is a sideview of a closure device including a fiber optic ring as a energy delivery device.
Figure 7B:
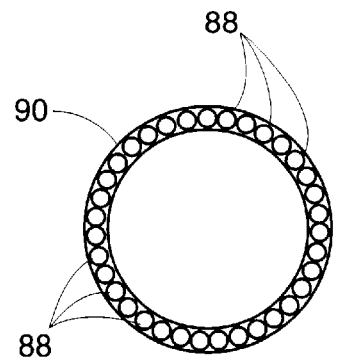
FIG. 7B is a cross section of the fiber optic ring of FIG. 7A.

The energy delivery device 28 may also be a wave guide 88 for delivery of UV, visible light or laser energy as illustrated in FIG. 7A. The closure device 10 includes a waveguide collar 90. FIG. 7B illustrates a cross section of the waveguide collar 90. A plurality of waveguides 88 are arranged circumferentially around the collar. The light is provided to the waveguides 88 through a cable 92 coupled to a light source 94.

The energy delivery device 28 may also be an electrode for delivering RF energy. The electrode can be a ring electrode encircling the body 12 as illustrated in FIG. 1A or a more localized electrode as illustrated in FIG. 2. The RF supply wires are run through the body 12 and coupled to the energy source attachment port 30. Alternatively, RF energy may be delivered to the closure composition precursor via the guidewire 82. Other types of energy 10 can also be used, including those that deliver ultrasound, resistive heating, exothermic chemical heating, other forms of electromagnetic radiation, and frictional heating.

Referring again to FIG. 1A, one example of a position sensing mechanism 34 is a pressure port coupled to the position monitor attachment port 38 by a position lumen. The position monitor 40 is a pressure sensor coupled to the position sensor attachment port by tubing. As a result, an open channel is created between the pressure port and the pressure sensor allowing the pressure sensor to detect the pressure at the port. The pressure within the vessel 60 is elevated compared with the pressure in the surrounding tissue. As a result, the signal from the pressure sensor indicates whether the position port is located within or outside the vessel 60.

Figure 8A:
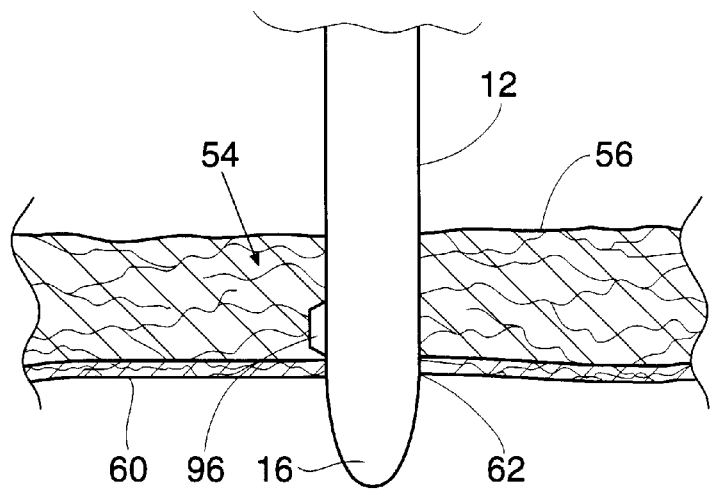
FIG. 8A is a sideview of a closure device with a contact switch as a position sensing mechanism.
Figure 8B:
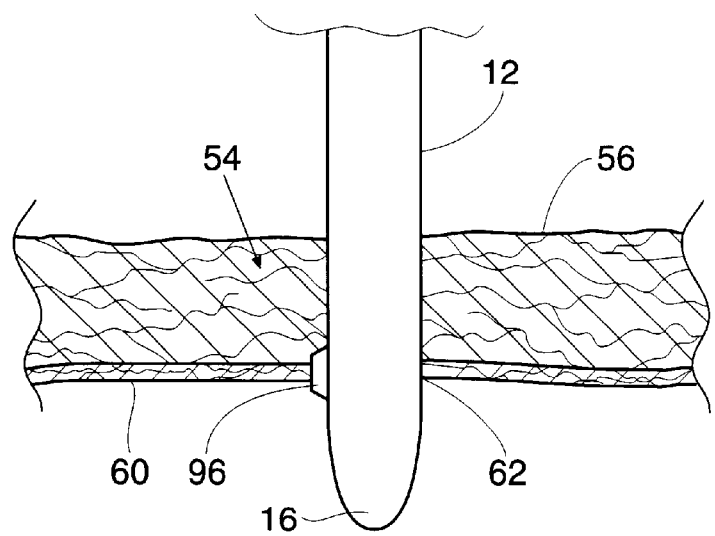
FIG. 8B is a sideview of a contact switch of FIG. 8A being compressed by the vessel wall.

The position sensing mechanism 34 can also be a contact switch 96 as illustrated in FIGS. 8A and 8B. The contact switch is coupled to the position monitor attachment port 38 by wires run through the body (not shown). When the switch 96 is in contact with the vessel wall the switch 96 closes and a circuit (not shown) is completed, however, when the switch 96 is not in contact with the vessel wall, the switch 96 remains open and the circuit is not completed. The circuit is monitored to determine the position of the closure device 10 relative to the vessel 60. Alternatively, the circuit can be coupled to the energy delivery device 24 such that the energy cannot be delivered unless the circuit is completed. In one embodiment, the device includes a mechanism which prevents the closure composition from being delivered if the position sensor is sensed to be within the vessel. As a result, energy will not be delivered unless the closure device 10 is properly positioned within the tissue site 54.

In a preferred embodiment, the closure device 10 includes two or more position sensors positioned around the closure device 10 where a reading that the sensor is outside the vessel occurs when all of the sensors are outside of the vessel. By having more than one position sensor around the closure device 10, false readings from one of the position sensors are reduced or avoided. For instance, if a single position sensing mechanism 34 is used, the sensing mechanism may become pressed against the vessel wall resulting in a pressure drop at the position sensing mechanism 34. The position monitor 40 would falsely provide a signal indicating that the position sensing mechanism 34 is outside the vessel 60. When a second position sensing mechanism is included, the second position sensing mechanism would still be exposed to the pressure within the vessel 60. As a result, the position monitor 40 would not provide a false signal. FIGS. 9A and 9B illustrate a closure device 10 with two position sensing mechanisms. In FIG. 9A, two pressure ports are coupled to a single position lumen. In FIG. 9B, each pressure port is coupled to a separate position lumen but both position lumens are coupled to the same tubing before the tubing is coupled to the pressure sensor.

When the position sensing mechanism 34 is a contact switch or a pressure port, the position sensing mechanism 34 is preferably positioned at least 25 mm from the distal end 16. This positioning assures that the distal end 16 of the closure device 10 remains within the vessel 60 when the closure device is positioned to deliver the closure composition precursor. This feature reduces the risk of delivering the closure composition precursor to an improper location on the vessel or within the vessel.

Figure 9C:
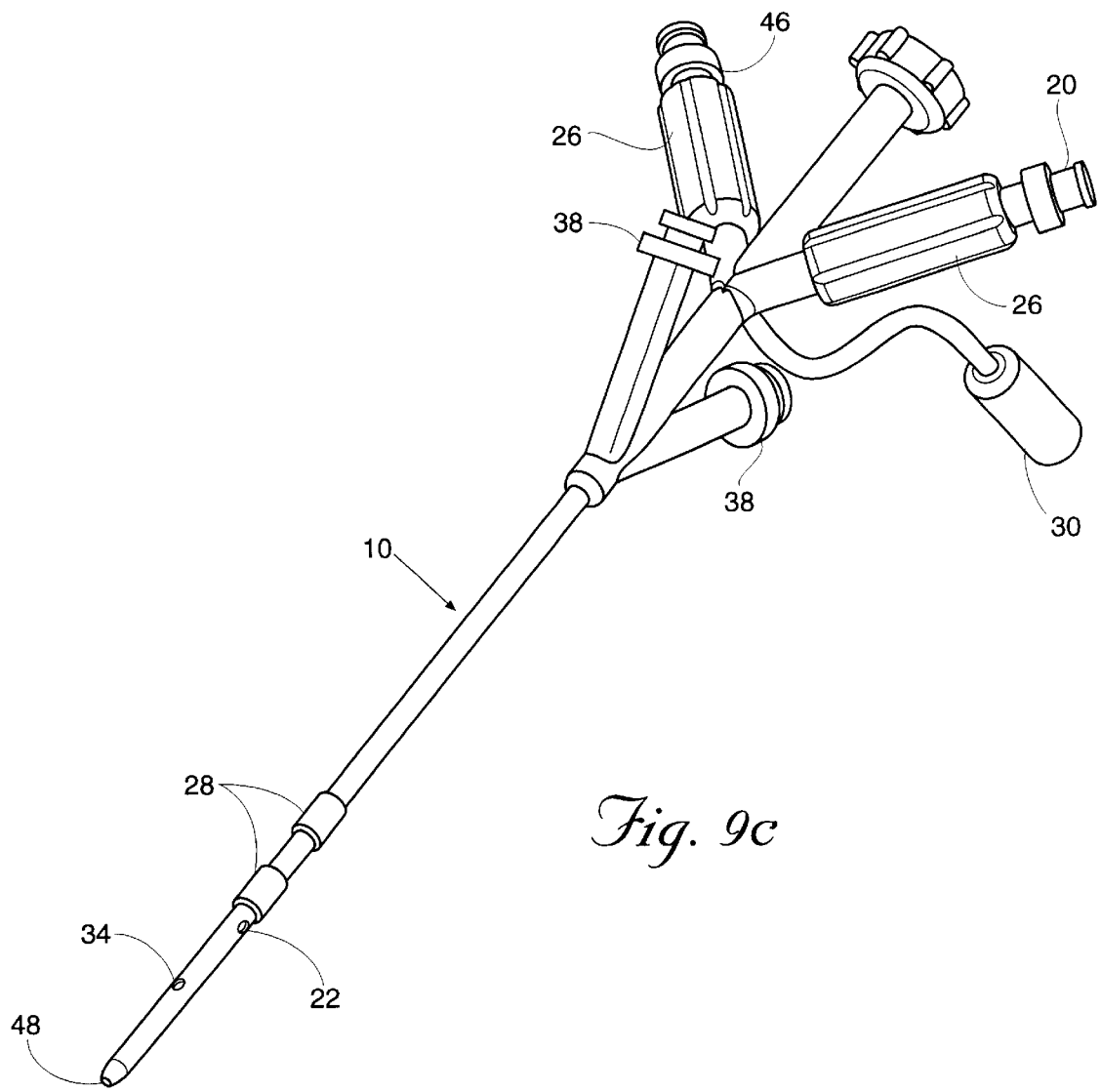
FIG. 9C illustrates a closure device with a plurality of pressure ports and first and second closure lumens.

FIG. 9C illustrates another embodiment of the closure device 10 according to the present invention. The closure device 10 includes a plurality of pressure ports 34 and a first precursor entrance port 20 and a second precursor entrance port 46. An energy delivery port 30 is coupled to a plurality of energy delivery devices 28. The closure device 10 includes a guidewire lumen 48 for use with the method described in FIGS. 6A–6G.

Figure 10A:
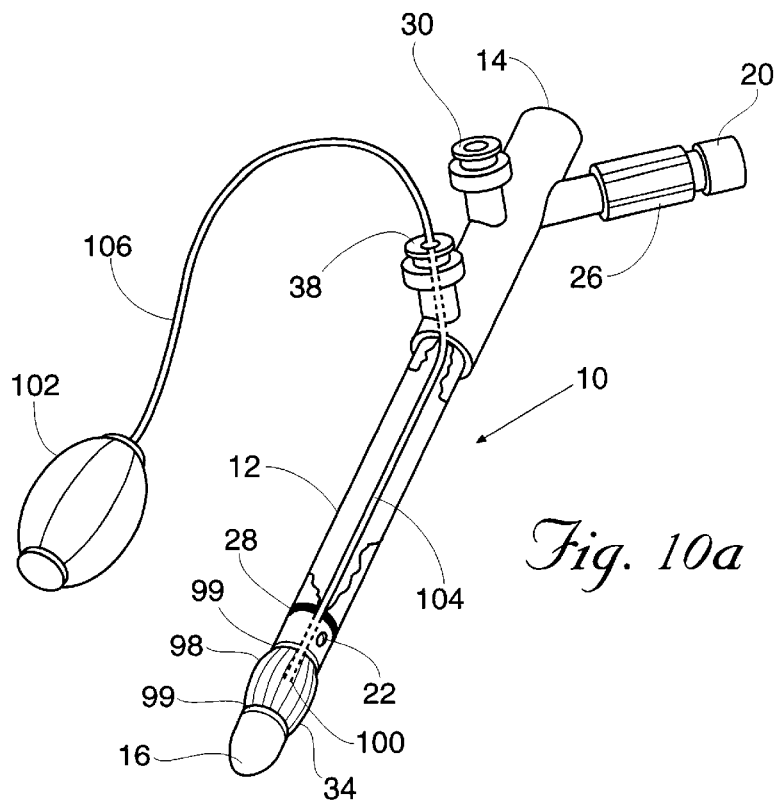
FIG. 10A is a sideview of a closure device including a balloon as the position sensing device.
Figure 10B:
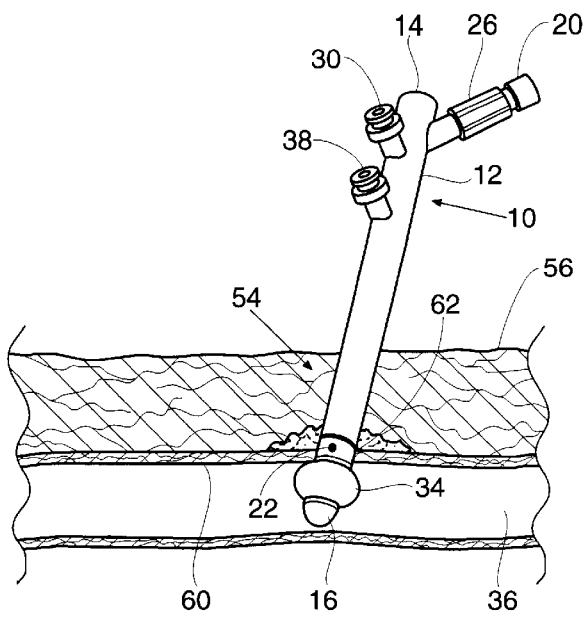
FIG. 10B illustrates the closure device of FIG. 10A disposed within a vessel.

FIGS. 10A and 10B illustrate another position sensing mechanism 34. A balloon 98 is coupled to the distal end 16 of the closure device 10 by a first and second retaining collar 99. The balloon is positioned over an inflation port 100. The balloon is coupled to an inflation bulb 102 by an inflation lumen 104 and an inflation tube 106. The balloon 98 is deflated when the closure device 10 is positioned within the vessel 60. Once the balloon 98 enters the vessel 60, the balloon 98 is inflated to a diameter greater than the diameter of the sheath 52 and thus the puncture 62. The closure device 10 is then withdrawn until the resistance of the balloon against the puncture 62 is felt as illustrated in FIG. 10B. The resistance indicates that the precursor exit port 22 is outside the vessel 60 and properly positioned for application of the closure composition precursor.

Figure 11:
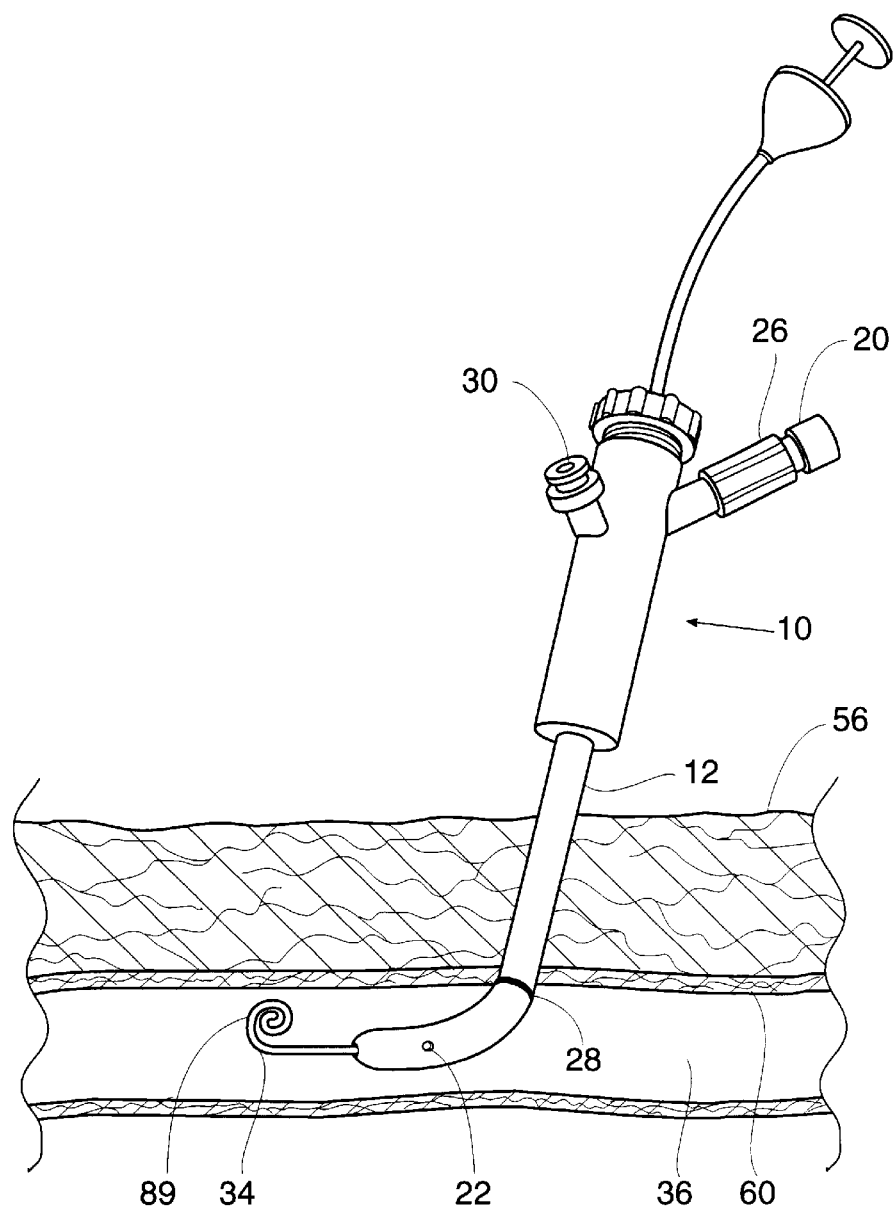
FIG. 11 illustrates a position sensing mechanism in the form of a curved wire positioned within the vessel lumen.

FIG. 11 illustrates yet another embodiment of a position sensing mechanism 34. According to this embodiment, a curved wire 89 is positioned within the vessel. As the closure device 10 is withdrawn, resistance is felt when the curved wire 89 is pushed up against the interior of the vessel lumen. The closure precomposition ports are positioned such that when the resistance is felt, the precomposition ports are known to be positioned outside of the vessel.

Each position sensing mechanism 34 can be distally positioned 0.5–30 mm from the precursor exit port 22 and more preferably 3.0–9.0 mm from the precursor exit port 22. These distances allow the closure composition precursor to be reliably delivered outside the vessel 60 once the closure device 10 is positioned for delivery of the closure composition precursor.

A variety of additional sensors may be used in combination with the present invention. For example, temperature sensors may be positioned adjacent the distal end 16 of the closure device 10 for detecting the temperature adjacent the distal end 16. The temperature sensors may be a thermocouple positioned on the surface of the body 12 (not shown) and hardwired to electrical contacts within a sensor monitor attachment port (not shown). These sensors are useful for regulating the amount of energy being delivered to the vessel 60 and tissue adjacent the closure device 10 and for preventing tissue damage and ablation due to excess heat application.

Impedance sensors may also be employed when RF is used in order to monitor the amount of energy being delivered to the tissue.

Figures 12A, 12B:
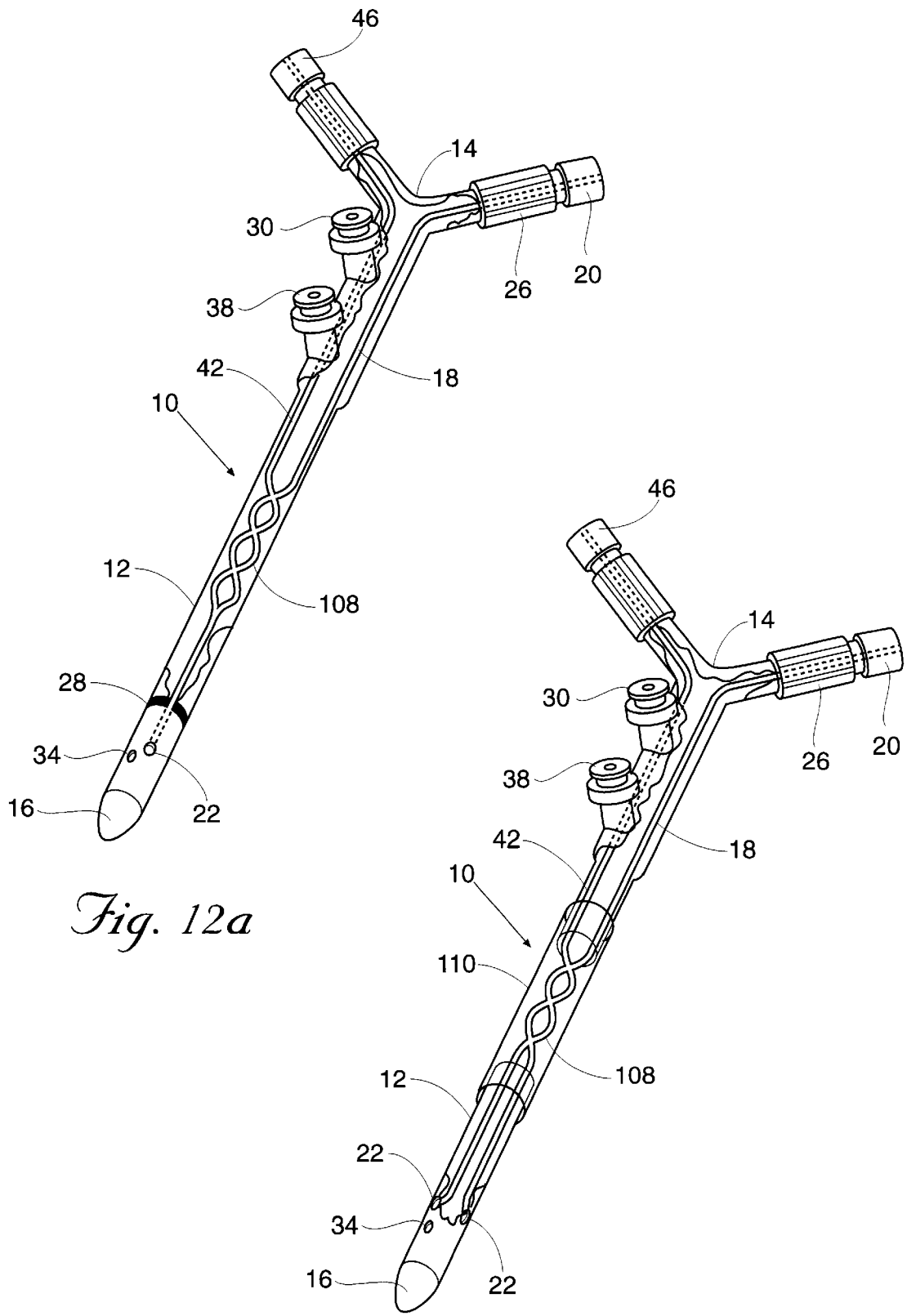
FIG. 12A is a cross section of a closure device with a plurality of closure lumens and a static mixer.
FIG. 12B is a cross section of a static mixer which is a removable cartridge.

When the closure composition precursor is formed of two or more components, the closure device 10 can optionally include a static mixer 108 for mixing different closure composition precursor components before the closure composition precursors exit the precursor exit port or ports 22. FIG. 12A illustrates a static mixer 108 incorporated into the closure device 10. The first closure lumen 18 and the second closure lumen 42 intersect at least one time before terminating in at least one precursor exit port 22. The static mixer can also be a cartridge 110 incorporated into the body 12 of the closure device 10 as illustrated in FIG. 12B. The intersection of the first and second lumens assures that the first and second closure composition precursors are mixed before reaching the at least one precursor exit port 22.

The configuration of precursor exit ports can also serve to assure adequate mixing of the first and second closure composition precursors. As illustrated in FIG. 13, the precursor exit ports 22 corresponding to the first closure composition alternate with the precursor exit ports corresponding with the second closure composition 112. As a result, the first and second closure composition precursors are mixed outside the closure device 10.

Figure 14A:
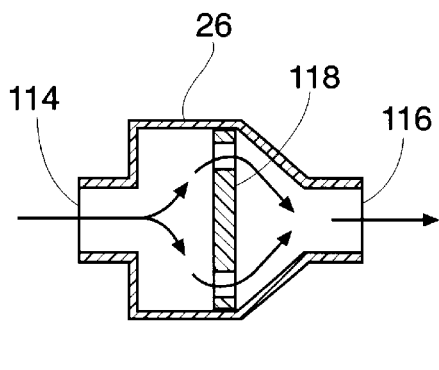
FIG. 14A is a cross section of an anti-backflow valve.
Figure 14B:
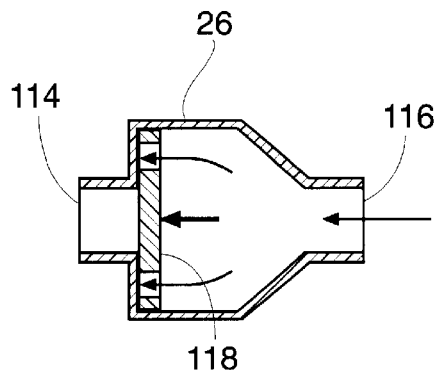
FIG. 14B is a cross section of an anti-backflow valve.

A backflow valve 26 which is suitable for use in a closure lumen is illustrated in FIGS. 14A and 14B. The valve 26 has a composition entrance 114 and a composition exit 116. FIG. 14A illustrates that when a fluid flows from the entrance 114 to the exit 116, a diaphragm 118 slides forward to allow the closure composition precursor to flow freely through the valve 26. FIG. 14B illustrates that when a fluid flows from the exit 116 to the entrance 114, the fluid places pressure against the backside of the diaphragm 118 causing the diaphragm 118 to slide against the entrance 114 sealing the entrance 114 and preventing a flow of fluid through the valve 26.

Figure 15A:
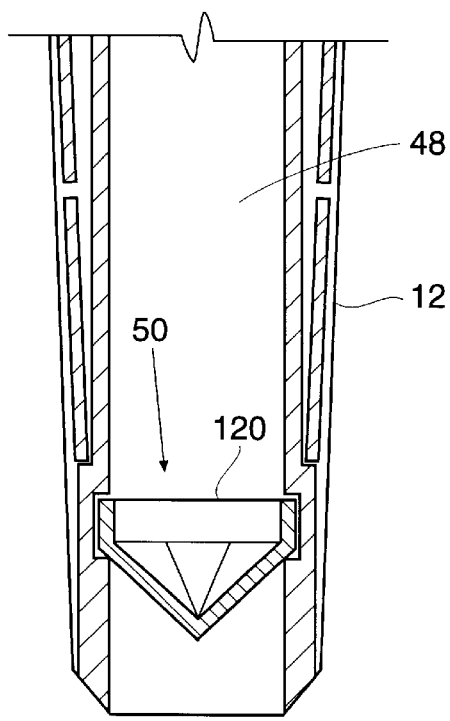
FIG. 15A illustrates a flapper valve disposed within the distal end of a closure device.
Figure 15B:
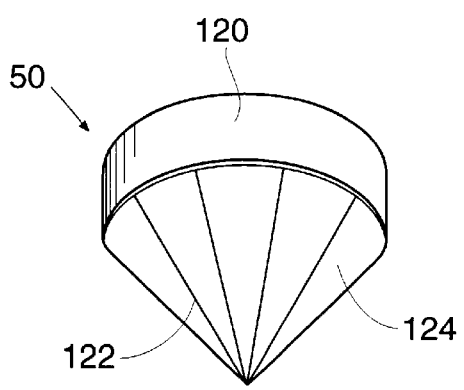
FIG. 15B is a sideview of a flapper valve.

An example of a suitable backflow valve 50 for use in the central lumen 48 adjacent the distal end of the device is a flapper valve 120 as illustrated in FIGS. 15A and 15B. Examples of backflow valves for the central lumen which may be positioned adjacent the proximal end of the device include, but are not limited to, duckbill valves, hemostasis valves, and Tuhoy-Bourse valves. The flapper valve 120 is preferably formed of an elastomeric material such as medical grade silicone rubber. The configuration, as illustrated by FIG. 15B, may be a cylindrical section transitioning into a conical portion. The conical portion has a series of slits 122 which allow various implements to pass through the valve 50. The thickness of the flaps 124 and the flexibility of the elastomeric material will be balanced to provide memory sufficient to close the puncture as the implements are withdrawn and provide a fluid seal. Blood pressure against the outer surface of the cone will cause the flapper valve 50 to close more tightly.

The body 12 is formed of any suitable, relatively flexible material. Suitable materials include, but are not limited to, polyethylene, PEBAX, polytetrafluroethylene (TEFLON) and polyurethane.

A variety of different closure composition precursors and non-fluent closure compositions can be used in the present invention. The fluent closure composition precursor and non-fluent closure composition should be biocompatible and preferably bioresorbable. The closure composition should be also capable of forming a strong puncture seal and be able to seal larger sized vessel punctures, e.g., punctures formed by 8 french or larger needles. Examples of closure compositions that can be used with the device and method of the present include, but are not limited to sealants and adhesives produced by Protein Polymer Technology; FOCALSEAL produced by Focal; BERIPLAST produced by Centeon (JV Behringwerke & Armour); VIVOSTAT produced by ConvaTec (Bristol-Meyers-Squibb); SEALAGEN produced by Baxter; FIBRX produced by CyoLife; TISSEEL AND TISSUCOL produced by immuno AG; QUIXIL produced by Omrix Biopharm; a PEG-collagen conjugate produced by Cohesion (Collagen); HYSTOACRYL BLUE produced by Davis & Geck; NEXACRYL, NEXABOND, NEXABOND S/C, and TRAUMASEAL produced by Closure Medical (TriPoint Medical); OCTYL CNA produced by Dermabond (Ethicon); TISSUEGLU produced by Medi-West Pharma; and VETBOND produced by 3M. Examples of two part closure compositions which may be used are listed in Table 1.

TABLE 1

| CLASS OF ADHESIVE | PART A | PART B |
| --- | --- | --- |
| (Meth) Acrylic (redox initiated) | (Meth) acrylic functional monomers and oligomers with oxidant initiator | (Meth) acrylic functional monomers and oligomers with reductant initiator |
| Polyurethane | Poly isocyanate | Hydrocarbon polyol, polyether polyol, polyester polyol |

TABLE 1-continued

| CLASS OF ADHESIVE | PART A | PART B |
|---|---|---|
| Polyurea | Poly isocyanate | Hydrocarbon polyamine, polyether polyamine |
| Ionomer | Polyvalent metal cation | Acrylic acid (co) polymer, alginate |
| Epoxy | Epoxy resin | Aliphatic polyamine, catalyst |
| Protein/dialdehyde | Gelatin | Glutaraldehyde |

Another aspect of the present invention relates to a method for improving the adhesiveness of a surface of living tissue by treating the tissue surface with a form of energy which thermally modifies the tissue surface and renders the surface more readily bonded or adherent to tissue adhesives, sealants, glues and the like. The thermal modification preferably includes blanching the tissue surface. The thermal modification is believed to reduce the water content at the tissue surface, remove materials at the tissue surface which interfere with the adhesiveness of tissue surfaces to sealants and adhesives, change the topography at the tissue surface, and preferably increase the surface area at the tissue surface, all of which serve to increase the tissue surface's ability to adhere sealants and adhesives.

In one embodiment, the method includes exposing a tissue surface to be so treated, which optionally includes the action of forming new tissue surfaces such as by cutting tissue with a scalpel or tool, or by introducing a medical instrument into previously continuous tissue such as with a cannula, introducer, catheter, or trocar, to provide new tissue surface(s) surrounding the instrument. For example, this step is encompassed by the step of introducing a closure device of the present invention into tissue.

After a tissue surface to be treated has been exposed, the tissue surface is contacted with a source of energy which functions to heat the surface of the tissue. Examples of suitable forms of energy include but are not limited to electromagnetic energy (RF energy, light, and microwave energy), ultrasound, and other thermal heat sources. In one particular embodiment, RF energy may be delivered to the tissue surface from a metallic electrode (monopolar) of any convenient shape, such as ring or needle. In another particular embodiment, RF energy is delivered through a saline solution provided by a microporous membrane (MPM). In yet another particular embodiment, the RF energy has an intermittent and variable waveform, such as so-called "coagulation" waveforms, which can serve to increase the bondability of the tissue surface.

Energy is applied until a degree of "blanching" has been achieved and the ability to bond to the tissue surface is increased. It is believed that the energy thermally modifies the tissue surface and causes the tissue to be more adherent to sealants and adhesives, such as closure composition used in the present invention.

While the pretreatment method is being described herein with regard to its use in combination with a closure device of the present invention, it is envisioned that the pretreatment method is a tissue priming method which may be used to enhance the adhesiveness of any tissue surface to which a tissue glue or sealant is to be applied and thus may be used with other methods for joining tissues other than those described in this application. It is believed that this method can be beneficially used in a variety of protocols or procedures which use non-mechanical agents such as glues, adhesives and sealants to join tissue. It is also believed that this method can be beneficially used in protocols or procedures which use mechanical mechanisms, such as mechanical fasteners, to join tissue. Further, it is believed that the pretreatment method will be beneficial for improving bonding strength to and between tissue surfaces in procedures relying on chemical adhesion, including covalent bonding, as well as mechanical interlocking.

Figure 16:
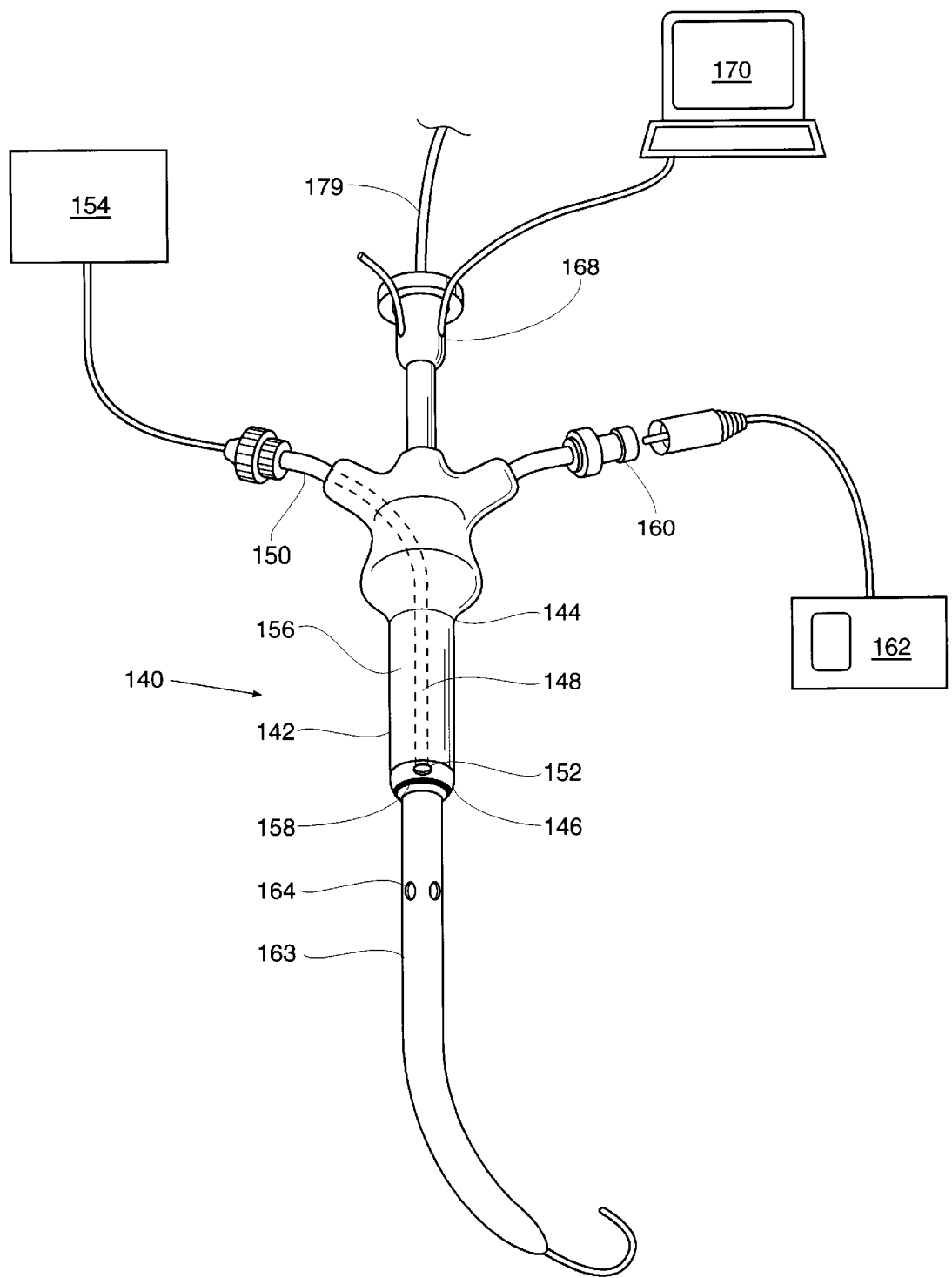
FIG. 16 illustrates an embodiment of a closure device which can thermally pretreat tissue prior to the delivery of a closure composition in order to enhance the adhesiveness of tissue to the closure composition.

FIG. 16 illustrates an embodiment of a closure device 140 which includes an energy source for pretreating tissue prior to the delivery of a closure composition in order to enhance the adhesiveness of tissue to the closure composition. The closure device 140 may be used to seal a puncture in a vessel such as a femoral artery. The closure device 140 includes an sealer/dilator 142 with a proximal end 144 and a distal end 146 which serves as a sealer and tissue dilator. The surface of the sealer/dilator 142 is preferably made of a non-stick material, such as TEFLON, or coated with a biocompatible lubricant. Positioned within the sealer/dilator 142 are one or more closure lumens which extend from adjacent the proximal end 144 of the device to the distal end 146 of the device for introducing a closure composition precursor adjacent the vessel puncture site. Illustrated in FIG. 16 is a closure device 140 with a single closure lumen 148 with a precursor entrance port 150 and at least one precursor exit port 152 adjacent the distal end 146. The precursor entrance port 150 is preferably removably coupleable to a closure composition precursor source 154 for supplying the closure composition precursor to the closure device 140. The closure lumen 148 may optionally contain an anti-backflow valve 156 to prevent blood from flowing into the closure lumen 148 from the vessel.

The closure composition precursor can be formed of one or more fluent materials that can be flowed from the closure composition precursor source 154 to adjacent the device distal end 146 through the closure lumen 148, such as the closure composition precursors described in this application. The fluent closure composition precursor is transformed into a non-fluent closure composition in situ to effect closure of the puncture.

The sealer/dilator includes an energy delivery device 158 adjacent the distal end 146 for pretreating the tissue prior to delivering the closure composition precursor to the tissue. The energy delivery device 158 may be designed to deliver one or more different types of energy including but not limited to electromagnetic radiation (RF, microwave, ultraviolet, visible light, laser), ultrasound, resistive heating, exothermic chemical heating, and frictional heating. The closure device 140 also includes an energy source attachment mechanism 160 for placing the energy delivery device 158 in energetic communication with an energy source 162.

A plugging catheter 163 sized to fit within a vessel lumen extends from the distal end 146 of the sealer/dilator 142. In one embodiment, the sealer/dilator is actually a cylindrical, tubular element having a lumen within which the plugging catheter can be moved axially. The plugging catheter 163 includes at least one position sensing mechanism 164 for indicating whether the position sensing mechanism 164 is located within or outside of the vessel 166. The position sensing mechanism 164 should be positioned on the plugging catheter 163 distal to the precursor exit port 152 so that when the position sensing mechanism 164 is outside the vessel the precursor exit port 152 is also outside the vessel.

FIG. 16 illustrates the closure device 140 with dual position sensing mechanisms 164. As illustrated, the closure device 140 may also include a position monitor attachment port 168 for coupling the position sensing mechanism 164 to a position monitor 170. Examples of a position sensing mechanisms include, but are not limited to, a pressure port and an electrical contact switch.

The sealer/dilator 142 and plugging catheter 163 also include a guidewire lumen configured to accommodate a guidewire 179. The guidewire lumen can include an anti-backflow valve or hemostasis valve.

Other sensors (not shown) may also be positioned on the plugging catheter 163 or the sealer/dilator 142. For instance, a temperature sensor for measuring temperature adjacent the distal end 146 of the sealer/dilator 142 and/or an impedance sensor may be positioned at the distal end 146 of the sealer/dilator 140.

The sealer/dilator 142 can include two or more closure lumens for the introduction of closure composition precursor. For example, a second closure lumen may be coupled to a second closure composition precursor source by a second precursor entrance port. The second closure lumen may also contain an anti-backflow valve to prevent blood flow through the second closure lumen.

The closure composition precursor may be introduced adjacent the vessel puncture as a single composition through a single closure lumen. Alternately, a first composition may be introduced through the closure lumen and a second composition can be introduced through the second closure lumen. The first and second compositions can be the same or different and can be introduced simultaneously or at different times. The first and second compositions may interact to accelerate the transformation to the non-fluent closure composition at the tissue site, for example, by reacting with each other or by one catalyzing the solidification of the other.

In a preferred embodiment, the closure device also includes an energy source for applying energy to the closure composition precursor to accelerate its transformation into the non-fluent closure composition. The transformation of the fluent precursor to a non-fluent closure composition may be the result of a phase change (i.e. solidification) of the precursor or a chemical modification of the precursor. For example, the precursor may be formed from multiple components which react with each other, optionally accelerated by a catalyst or energy. Alternatively, the precursor may be formed from a single component which reacts with itself, also optionally accelerated by a catalyst or energy.

In embodiments where energy is applied, the energy delivery device on the elongated body or an additional energy delivery device is used to deliver one or more different types of energy including but not limited to electromagnetic radiation (RF, microwave, ultraviolet, visible light, laser), ultrasound, resistive heating, exothermic chemical heating, and frictional heating which serves to accelerate the conversion of the closure composition precursor to a non-fluent closure composition.

Figure 17:
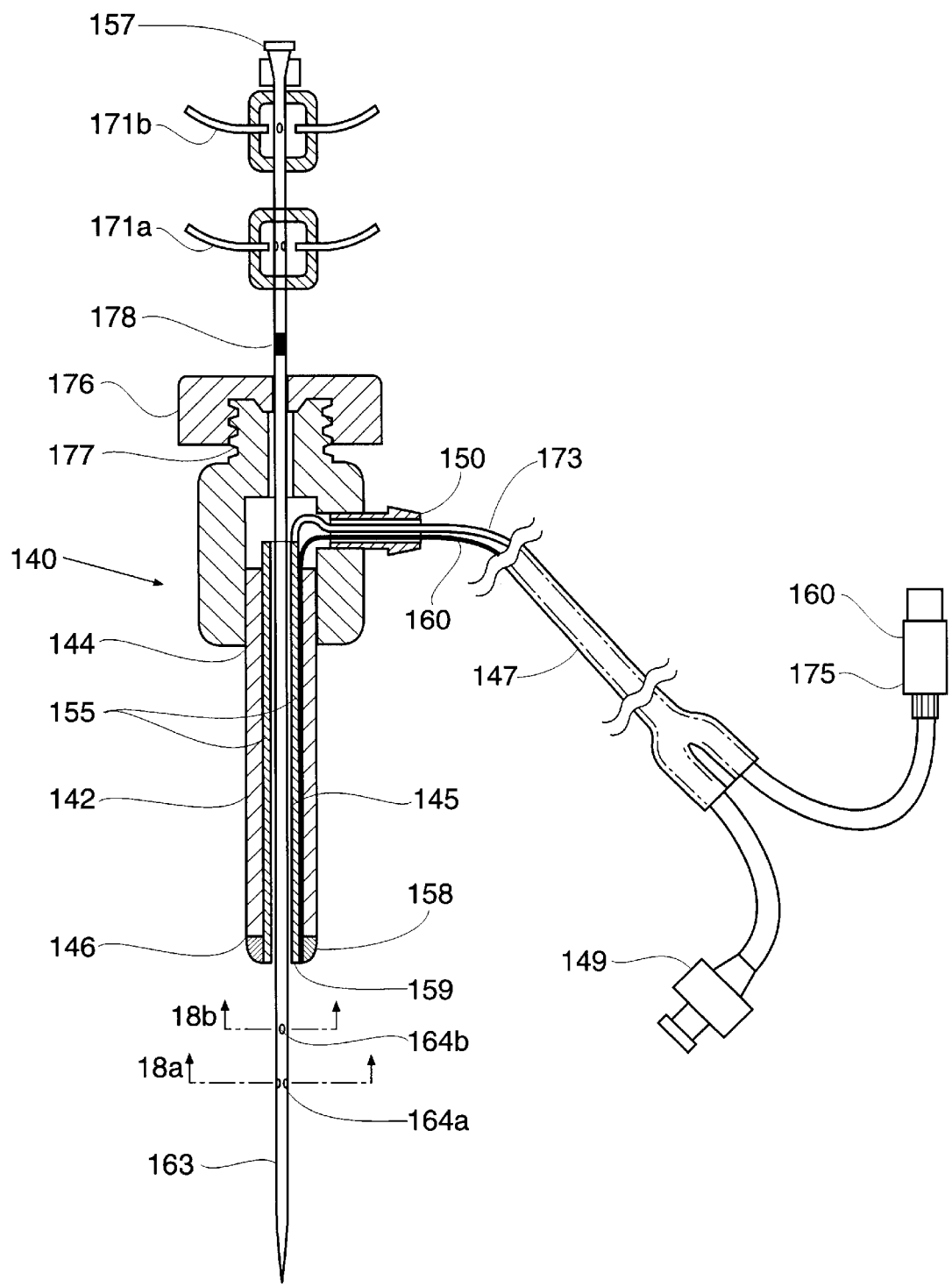
FIG. 17 illustrates a cross section of one possible embodiment of a closure device according to the present invention which includes an energy source for pretreating tissue.

FIG. 17 illustrates a cross section of one possible embodiment of a closure device according to the present invention which includes an energy source for pretreating tissue. As illustrated, the closure device 140 includes an sealer/dilator 142 with a proximal end 144 and a distal end 146 which serves as a sealer and tissue dilator. The surface of the sealer/dilator 142 is preferably made of a non-stick material, such as TEFLON, or coated with a biocompatible lubricant. Positioned within the sealer/dilator 142 is a central lumen 145. The central lumen serves as a lumen for a guidewire and plugging catheter. The lumen also serves as a lumen for the closure composition precursor. As illustrated, the central lumen 145 is also connected to a precursor entrance port 150 adjacent the proximal end 144 of the device and extends to a precursor exit port 152 adjacent the distal end 146. The precursor entrance port 150 is preferably removably coupleable to a closure composition precursor source (not shown) for supplying the closure composition precursor to the closure device 140. Tubing 147, such as TYGON tubing, with a valve 149 may be attached to the precursor entrance port 150 for facilitating attachment of a closure composition precursor source (not shown).

The sealer/dilator includes an energy delivery device 158 adjacent the distal end 146 for pretreating the tissue prior to delivering the closure composition precursor to the tissue. The energy delivery device 158 is energetically connected via a conductive metal tube 155 and a wire 151 to an energy source attachment mechanism 160 for placing the energy delivery device 158 in energetic communication with an energy source (not shown).

The sealer/dilator also includes threading 177 adjacent its proximal end for attaching a hemostasis/lock valve 176 to the sealer/dilator distal end.

A plugging catheter 163 sized to fit within a vessel lumen extends through the central lumen 145 and out the distal end 146 of the sealer/dilator 142. The proximal end of the plugging catheter 163 includes a guidewire Luer 157 for positioning a guidewire within a guidewire lumen 169. The plugging catheter 163 can optionally include a locating mark 178 which can be used to indicate how far the plugging catheter 163 is extending from the distal end of the sealer/dilator 142.

The plugging catheter 163 includes first and second position sensing mechanisms 164A, 164B for indicating whether the first and second position sensing mechanisms 164A, 164B are located within or outside of the vessel. As can be seen, the first position sensing mechanism 164A is distal relative to the second position sensing mechanism 164B. This enables the plugging catheter to be positioned such that the first position sensing mechanism 164A is inside the vessel and the second position sensing mechanism 164B is outside the vessel.

Figure 18A:
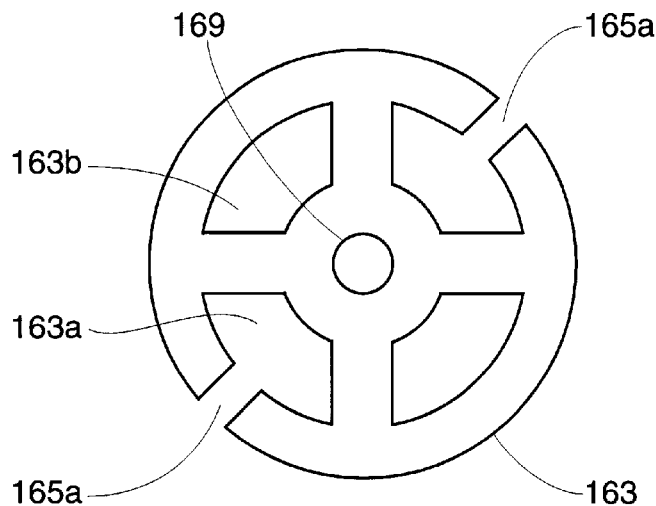
FIG. 18A illustrate a cross section of a first pressure port.
Figure 18B:
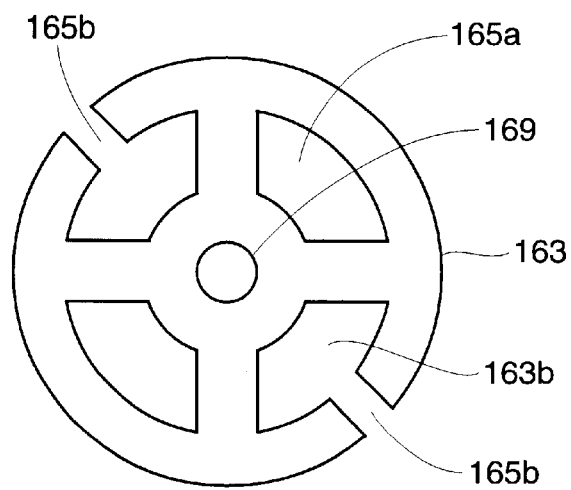
FIG. 18B illustrates a cross section of a second pressure port.

One example of a position sensing mechanism is a pressure port coupled to the position monitor attachment port by a position lumen. FIGS. 18A and 18B illustrate a cross section of the plugging catheter which includes two position sensing mechanisms. As illustrated in FIG. 18A, the first position sensor 164A includes a first position sensor lumen 163A and a pair of first pressure ports 165A. Also illustrated in FIG. 18A is the second position sensor lumen 163B of the second position sensor 164B. FIG. 18B illustrates a pair of second pressure ports 165B of the second position sensor 164B.

As illustrated in FIG. 17, the device also includes marker port capillary tubes 171A, 171B attached to the first and second position sensor lumens 163A and 163B respectively.

As can be seen from FIGS. 18A and 18B, the first and second pressure ports 165A, 165B are preferably angularly offset relative to each other so that the sensor ports will not be blocked by a same obstruction. Similarly, at least a pair of sensor ports is preferably used in each sensor mechanism so that a given sensor mechanism is not blocked by a single obstruction. These design features enhance the reliability of the sensor mechanisms.

Also illustrated in FIGS. 18A and 18B is a guidewire lumen 169 configured to accommodate a guidewire 179 running through the plugging catheter 163. The guidewire lumen can include an anti-backflow valve or hemostasis valve.

Other sensors may also be positioned on the plugging catheter 163. For instance, as illustrated in FIG. 17, a temperature sensor 159 for measuring temperature adjacent the distal end 146 of the sealer/dilator 142 may be positioned at the distal end 146 of the sealer/dilator 140. As also illustrated, the temperature sensor 159 is connected to a temperature sensor wire 173 which can be attached to a temperature sensor connector 175.

Figure 19A:
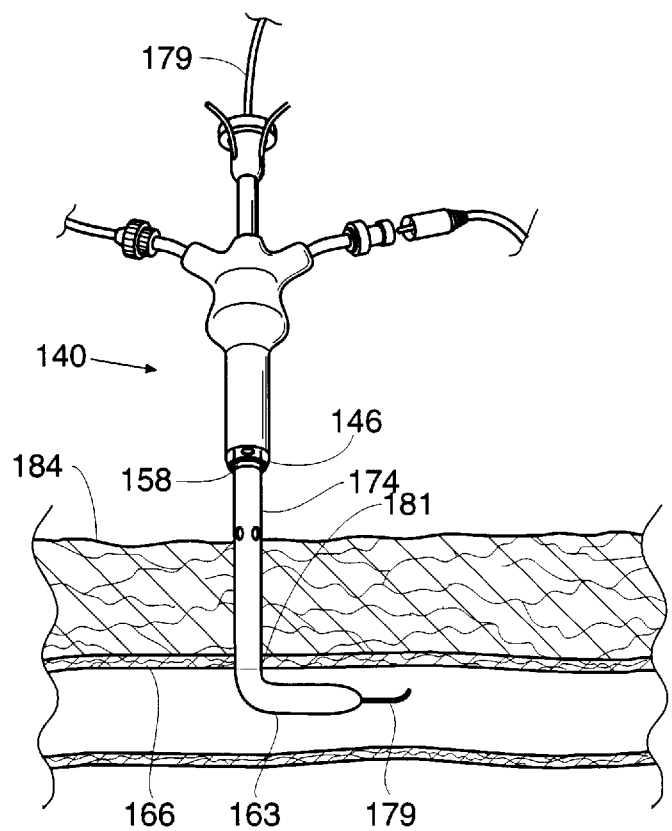
FIGS. 19A–19D illustrate a method of using the closure device illustrated in FIG. 16.

FIGS. 19A–19D illustrate a method of using the closure device 140 illustrated in FIG. 16. As illustrated in FIG. 19A, the guidewire 179 is thread within the guidewire lumen of the closure device 140 and the plugging catheter 163 is pushed forward through the tissue site 184 until the position sensor 174 indicates that the position sensor 174 is within the vessel 166. The plugging catheter 163 of the closure device 140 preferably has the same or larger diameter as the sheath used in the surgical procedure. Since the puncture 181 has been dilated to the diameter of the sheath, this sizing reduces leakage of blood between the puncture 181 and the closure device 140.

Figure 19B:
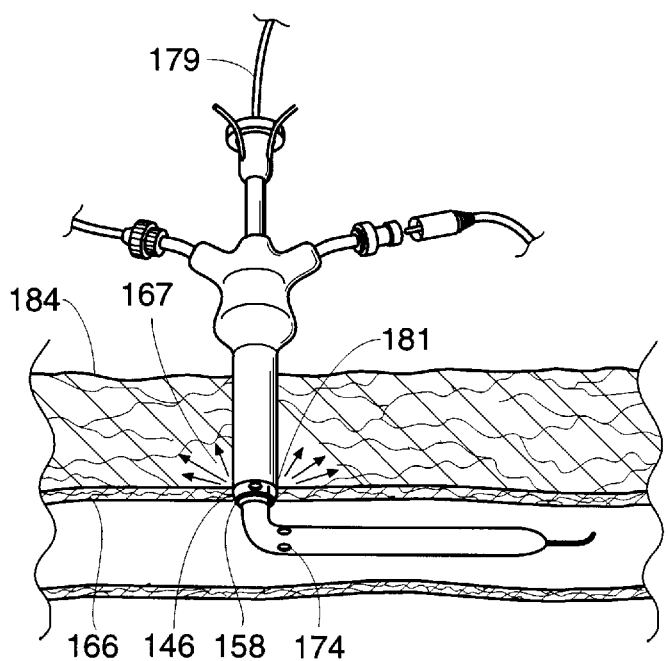

As illustrated in FIG. 19B, the closure device 140 is pushed into the tissue until the distal end 146 of the sealer/dilator 142 is adjacent the vessel 166. Because the distal end 146 of the sealer/dilator 142 is significantly larger than the puncture 181 in the vessel 166, resistance will be felt when the distal end 146 of the sealer/dilator 142 is pushed against the vessel 166. Energy 167 is then applied by the energy delivery device 158 to pretreat the vessel 166 and tissue adjacent the vessel.

Figure 19C:
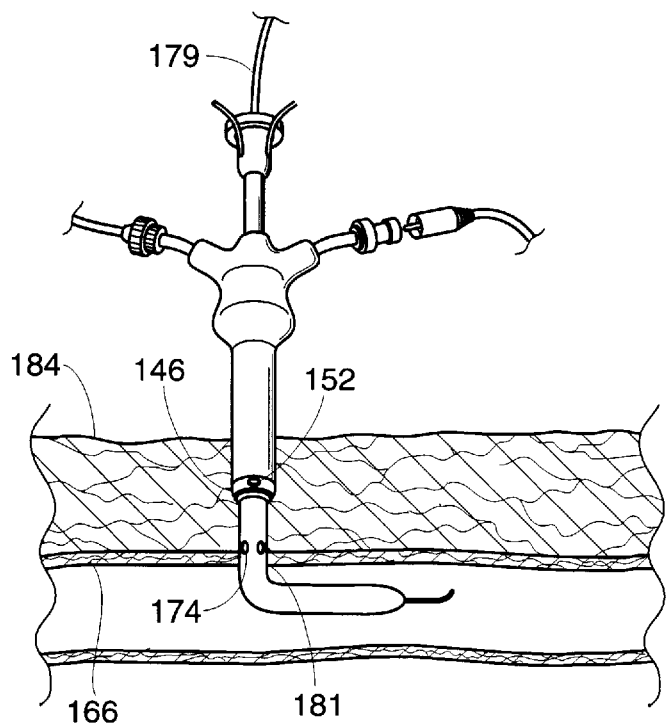

As illustrated in FIG. 19C, the closure device 140 is then slowly withdrawn from the vessel 166 until the position sensor 174 indicates that the position sensor 174 is located outside the vessel 166. Since the precursor exit port 152 is positioned proximally relative to the position sensor 166, withdrawal of the position sensor 166 from the vessel 174 assures that the precursor exit port 152 has been withdrawn from the vessel 166.

Figure 19D:
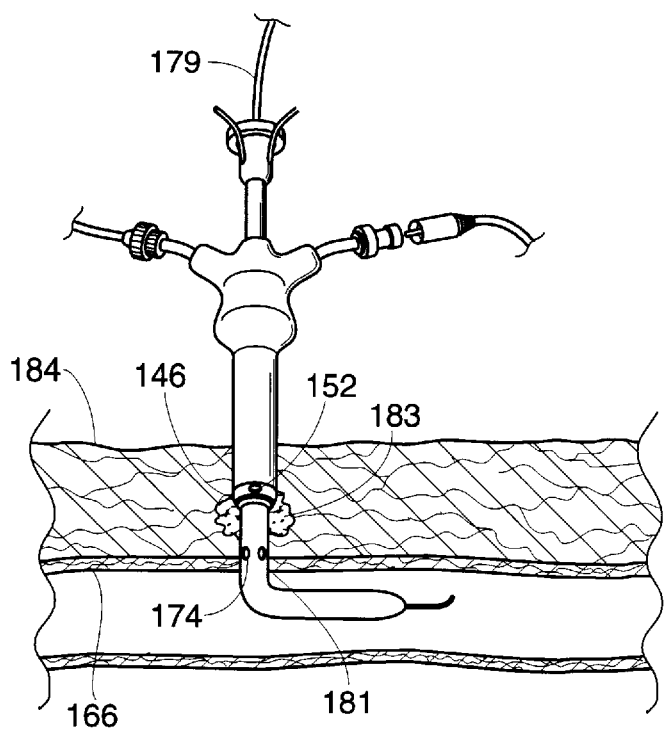

As illustrated in FIG. 19D, once the precursor exit port 152 is determined to be outside the vessel 166, a closure composition precursor 183 is delivered through the closure lumen 148 and out the precursor exit port 152 adjacent the vessel puncture 181.

Figure 20:
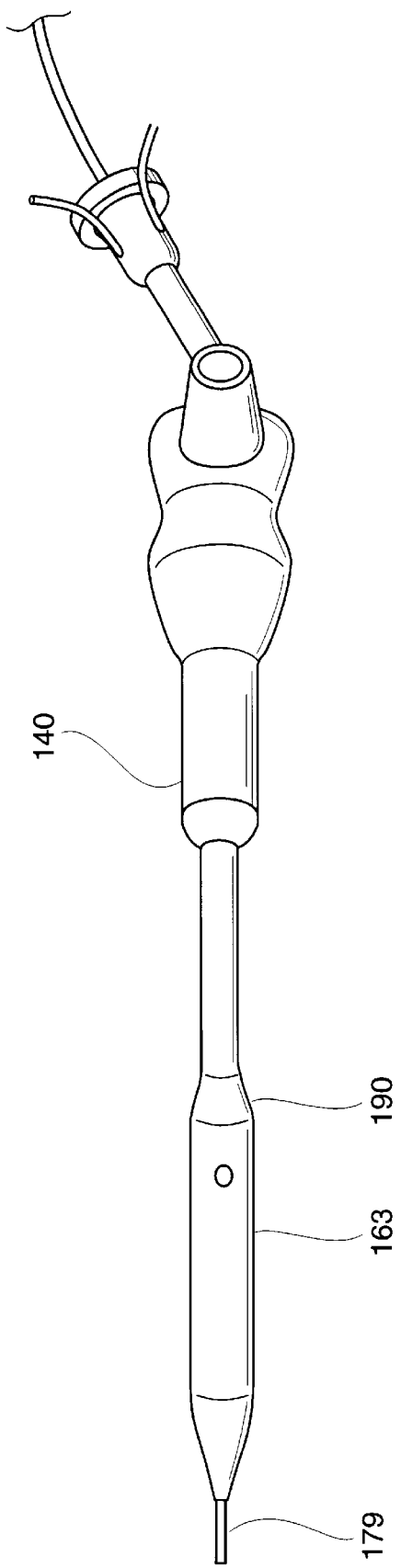
FIG. 20 illustrates a variation of the embodiment illustrated in FIG. 16 in which the sealer/dilator is a cylindrical, tubular element having a lumen within which the plugging catheter can be moved axially (←→)

FIG. 20 illustrates a variation of the embodiment illustrated in FIG. 16 in which the sealer/dilator is a cylindrical, tubular element having a lumen within which the plugging catheter can be moved axially (←—→). In this variation, the plugging catheter 163 may include a retraction locking mechanism 190 which limits how far the plugging catheter 163 may be withdrawn from the body of the patient through the sealer/dilator. As illustrated, the retraction locking mechanism 190 may be a member extending from the surface of the plugging catheter 163 which prevents the plugging catheter 163 from being withdrawn further.

Figure 21:
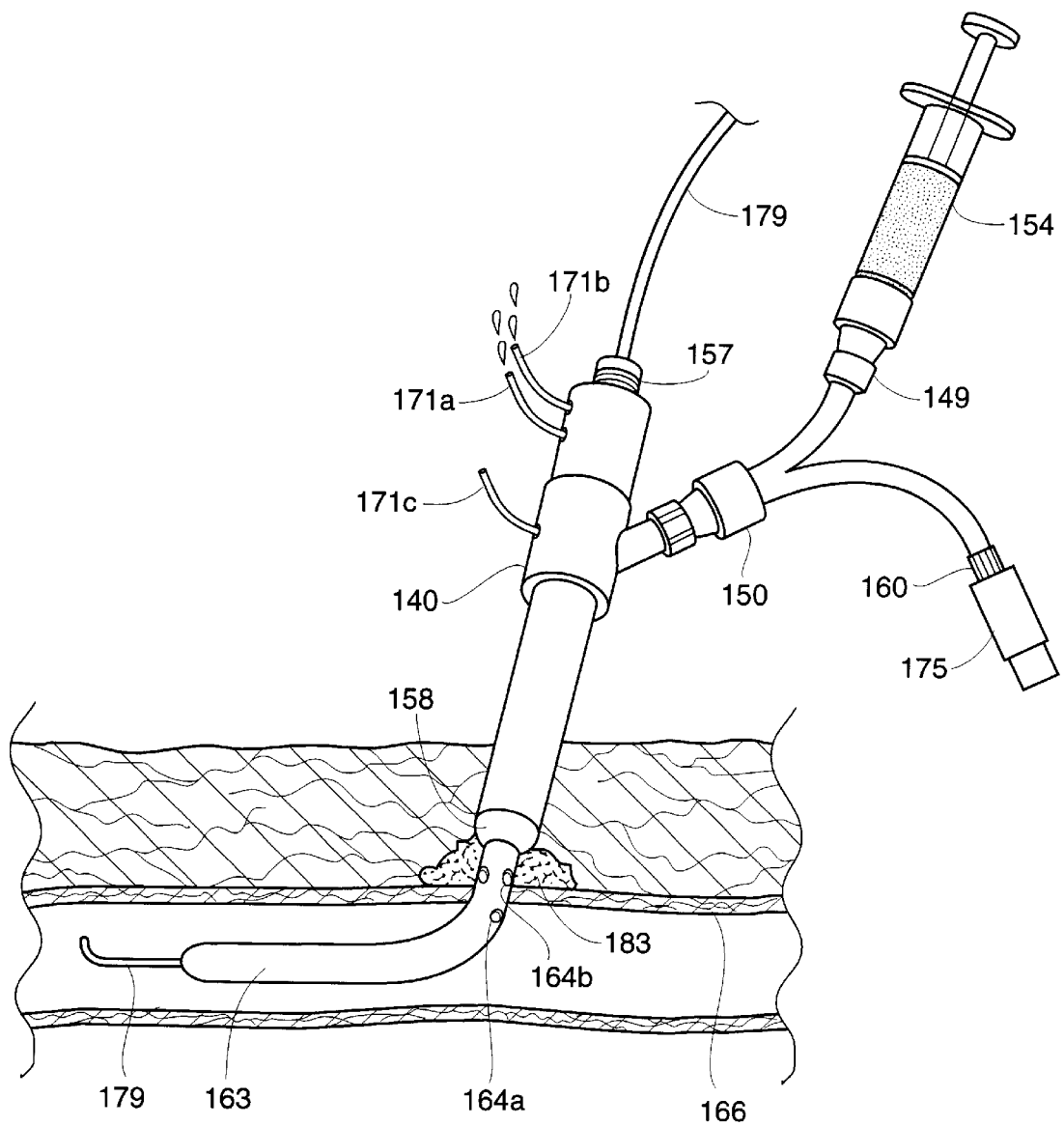
FIG. 21 illustrates a variation of the embodiment illustrated in FIG. 16 in which the position of the plugging catheter is fixed relative to the sealer/dilator.

FIG. 21 illustrates a variation of the embodiment illustrated in FIG. 16 in which the position of the plugging catheter is fixed relative to the sealer/dilator. As illustrated, the closure device 140 includes dual position sensing mechanisms 164A, 164B and dual capillaries 171A and 171B. Preferably, a closure composition is delivered adjacent to the vessel 166 when position sensing mechanism 164A is detected to be within the vessel and position sensing mechanism 164B is detected to be outside the vessel. The embodiment illustrated further includes a third position sensing mechanism 164C and capillary 171C which is used as a safety device to detect when the sealer/dilator is within the vessel.

Another aspect of the present invention relates to a method for improving the adhesiveness of a surface of living tissue by treating the tissue surface with a chemical agent which modifies the tissue surface and renders the surface more readily bonded or adherent to tissue adhesives, sealants, glues and the like. The chemical modification may optionally include a degree of surface denaturization, a reduction in the water content at the tissue surface, removal of materials at the tissue surface which interfere with the adhesiveness of tissue surfaces to sealants and adhesives, a change the topography at the tissue surface, and preferably an increase in the surface area at the tissue surface, all of which serve to increase the tissue surface's ability to adhere sealants and adhesives.

In one embodiment, the method includes exposing a tissue surface to be so treated, which optionally includes the action of forming new tissue surfaces such as by cutting tissue with a scalpel or tool, or by introducing a medical instrument into previously continuous tissue such as with a cannula, introducer, catheter, or trocar, to provide new tissue surface(s) surrounding the instrument. For example, this step is encompassed by the step of introducing a closure device of the present invention into tissue.

After a tissue surface to be treated has been exposed, the tissue surface is contacted with a suitable chemical agent. In one variation, a basic chemical agent (i.e., having a pH greater than 7) capable of modifying a tissue surface is used. Examples suitable basic chemical agents include but are not limited to aqueous sodium bicarbonate, aqueous sodium carbonate, water solutions or suspensions of alkali or alkali earth oxides and hydroxides, aqueous ammonia, water soluble amines such as alkanol amines, basic amino acids such as lysine and poly(lysine), aqueous sodium lysinate, and basic proteins such as albumin. In another variation, an acidic chemical agent (i.e., having a pH less than 7) having an osmolality above that of blood is used which is capable of modifying a tissue surface. In yet another variation, a chemical agent which can serve as a tissue etchant is used. Examples of suitable tissue etchants include, but are not limited to salicyclic acid, carboxylic acids, α-hydroxy carboxylic acids, and peroxides.

While the chemical pretreatment method is being described herein with regard to its use in combination with a closure device of the present invention, it is envisioned that the chemical pretreatment method is a tissue priming method which may be used to enhance the adhesiveness of any tissue surface to which a tissue glue or sealant is to be applied and thus may be used with other methods for joining tissues other than those described in this application. It is believed that this method can be beneficially used in a variety of protocols or procedures which use non-mechanical agents such as glues, adhesives and sealants to join tissue. It is also believed that this method can be beneficially used in protocols or procedures which use mechanical mechanisms, such as mechanical fasteners, to join tissue. Further, it is believed that the pretreatment method will be beneficial for improving bonding strength to and between tissue surfaces in procedures relying on chemical adhesion, including covalent bonding, as well as mechanical interlocking.

EXAMPLE

1. Procedure For Pretreating tissue

The following example provides an exemplary procedure for pretreating tissue with energy in order to enhance the adhesiveness of the pretreated tissue to an adhesive material.

Tissue samples were prepared by cutting beef flank steak into specimens about 35 mm long by 8 mm wide by 2 mm thick with a scalpel. Care was taken to ensure that the muscle fibrils were aligned lengthwise and the connective tissue between fibrils was intact. A set of 12 specimens was soaked in physiologic saline (NaCl; equal to about 0.9% wt.) for 30 minutes just prior to use. The saline soaked tissue was used as a model for living tissue, which would contain intercellular fluid and blood encountered during any tissue sealing or wound closure medical procedure.

An electrode comprised of a metal cap 6 mm in diameter and 2 mm deep on the end of a plastic wand was fitted with a thermocouple for measuring the temperature at the electrode surface. The electrode was connected to an Apical, Inc. (Menlo Park, Calif.) Radio Frequency (RF) generator.

Some of the tissue samples were treated with RF energy immediately prior to bonding with a tissue adhesive by the following method:

a) an aluminum pan containing a porous towel saturated with a physiologic saline solution was electrically connected to the RF generator via a standard electrosurgical grounding pad;

b) a tissue sample to be treated was laid onto the moist towel and the electrode wand touched endwise to one end of the tissue sample such that a circular area approximately 6 mm in diameter was in contact with the electrode and could be treated;

c) RF energy at a power of 10 watts in the frequency range of 300–700 kHz was applied to the electrode and to the tissue surface;

d) the electrode temperature was monitored during the application of energy and increased about 1–2° C./second in the temperature range of 25–65° C.;

e) the electrode treatment temperature was maintained at the desired level by the Apical RF Generator until treatment was manually stopped after the desired time at temperature; and f) the twelve energy treated tissue samples were set up in pairs to form six lap shear specimens. The energy treated tissue samples were then evaluated for the shear strength of the resultant lap bond. A standard gelatin/aldehyde two part tissue adhesive was spread onto the treated portion of one energy treated tissue sample and then compressed against a second energy treated tissue sample to form a lap shear specimen assembly. Bond area was calculated as the product of the bond width and the overlap of the tissue surfaces.

Lap shear bond strength evaluation was done on the six replicate specimen assemblies prepared for each set of control and RF treatment conditions. Bond strength was measure using a Chatillion Stress-Strain instrument. Bond strengths were taken as the average of the six replicates.

Experimental results from this experiment are tabulated in Table 2. As can be seen from the data presented in the table, pre-treatment of tissue with RF energy to a temperature of 50° C. for 5 seconds increased the average lap shear bond strength by 34% and increased the greatest observed strength in the sample population by 66%. These results demonstrate the efficacy of the pre-treatment method for increasing the bond strength of energy treated tissue relative to non-energy pretreated tissue.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

TABLE 2

| Sample | Bond Width, mm | Bond Overlap, mm | Bond Failure, × 100 lb | Lap Shear Bond Strength, g/cm$^2$ | AVG | STD DEV |
|---|---|---|---|---|---|---|
| Control | 9 | 10 | 58 | 23 | | |
| No Treatment | 14 | 8 | 42 | 10 | | |
| Saline Soak | 10 | 10 | 42 | 11 | | |
| | 9 | 10 | 44 | 22 | | |
| | 11 | 10 | 48 | 18 | | |
| | | | | | 215 | 47 |
| 50 C/5 sec | 9 | 10 | 41 | 27 | | |
| Pre-Treatment | 8 | 8 | 42 | 28 | | |
| Saline Soak | 7 | 8 | 60 | 46 | | |
| | 8 | 10 | 35 | 19 | | |
| | 7 | 11 | 68 | 41 | | |
| | 6 | 10 | 20 | 11 | | |
| | | | | | 290 | 131 |

What is claimed is:

1. A closure device for sealing a puncture in a body vessel comprising:

a sealer/dilator for dilating tissue adjacent a vessel puncture, the sealer/dilator including a proximal end and a distal end sized to not enter the vessel;

at least one closure composition precursor lumen within the sealer/dilator having an entrance port adjacent the proximal end of the sealer/dilator through which one or more fluent closure composition precursors can be delivered into the closure composition precursor lumen, a mixer which mixes the one or more fluent closure composition precursors within the closure composition precursor lumen, and an exit port adjacent the distal end of the sealer/dilator through which the one or more fluent closure composition precursors can be delivered outside the vessel adjacent the vessel puncture; and a plugging catheter for positioning within the vessel puncture, the plugging catheter extending distally from the sealer/dilator and including at least one position sensing mechanism such that the exit port of the closure composition precursor lumen is outside the vessel when the at least one position sensing mechanism is detected to be outside the vessel.

2. The closure device of claim 1 wherein the at least one position sensing mechanism is a pressure port.

3. The closure device of claim 1 wherein the at least one position sensing mechanism is a contact switch.

4. The closure device of claim 1 wherein the at least one position sensing mechanism is an inflatable balloon positioned adjacent the distal end and mounted over an inflation port.

5. The closure device of claim 1 wherein, the at least one position sensing mechanism is located 0.5–30.0 mm from the precursor exit port.

6. The closure device of claim 1 wherein, the at least one position sensing mechanism is located 3.0–9.0 mm from the precursor exit port.

7. The closure device of claim 1 wherein, the at least one position sensing mechanism is located 25 mm from the distal end.

8. A closure device for sealing a puncture in a body vessel comprising:
- a sealer/dilator for dilating tissue adjacent a vessel puncture, the sealer/dilator including a proximal end and a distal end sized to not enter the vessel,
- at least two closure composition precursor lumens within the sealer/dilator having entrance ports adjacent the proximal end of the sealer/dilator through which one or more fluent closure composition precursors can be delivered into the closure composition precursor lumen, and exit ports adjacent the distal end of the sealer/dilator through which the one or more fluent closure compositions can be delivered outside the vessel adjacent the vessel puncture, the at least two closure composition precursor lumens being connected at a junction within the sealer/dilator,
- a static mixer connected at the junction to cause mixing of closure composition precursor carried within each lumen, and
- a plugging catheter for positioning within the vessel puncture, the plugging catheter extending distally from the sealer/dilator and including at least one positioning sensing mechanism such that the exit port of the closure composition precursor lumen is outside the vessel when the at least one position sensing mechanism is detected to be outside the vessel.

9. The closure device of claim 1 wherein the closure composition precursor lumen includes at least one backflow valve.

10. The closure device of claim 1 further comprising a guidewire lumen.

11. A closure device for sealing a puncture in a body vessel comprising:
- a catheter having a proximal end and a distal end; and
- at least two closure composition precursor lumens within the catheter having entrance ports adjacent the proximal end of the catheter through which one or more fluent closure composition precursors can be delivered into the closure composition precursor lumen, and exit ports adjacent the distal end of the catheter through which the one or more fluent closure composition precursors can be delivered outside the vessel adjacent the vessel puncture, the at least two closure composition precursor lumens being connected at a junction within the catheter, and
- a static mixer connected at the junction to cause mixing of closure composition precursor carried within each lumen.

12. The closure device of claim 11, the closure device further including at least one position sensing mechanism positioned on the closure device such that the exit port of the closure composition precursor lumen is outside the vessel when the at least one position sensing mechanism is detected to be outside the vessel.

13. The closure device of claim 12 wherein the at least one position sensing mechanism is a pressure port.

14. The closure device of claim 12 wherein the at least one position sensing mechanism is a contact switch.

15. The closure device of claim 12 wherein the at least one position sensing mechanism is an inflatable balloon positioned adjacent the distal end and mounted over an inflation port.

16. The closure device of claim 12 wherein, the at least one position sensing mechanism is located 0.5–30.0 mm from the precursor exit port.

17. The closure device of claim 12 wherein, the at least one position sensing mechanism is located 3.0–9.0 mm from the precursor exit port.

18. The closure device of claim 12 wherein, the at least one position sensing mechanism is located 25 mm from the distal end.

19. The closure device of claim 11 wherein each of the at least two closure composition precursor lumens include at least two exit ports, the exit ports of the at least two lumens being alternatively positioned around the distal end of the sealer/dilator.

20. The closure device of claim 11 wherein the closure composition precursor lumen includes at least one backflow valve.

21. The closure device of claim 11 further comprising a guidewire lumen.

22. An assembly for introducing a closure material to seal a vessel puncture site, the closure material comprising a mixture of a first and a second fluid composition which, upon mixing, react to form a nonfluent closure composition, the assembly comprising:
- a catheter for passage through a tissue puncture and having a distal end, at least one fluid delivery port adjacent the catheter distal end to occupy a position adjacent the vessel puncture site, and a lumen in the catheter in fluid communication with the fluid delivery port;
- one or more dispensers in fluid communication with the catheter lumen for dispensing the first and second fluid compositions into the catheter lumen; and
- an actuator for causing the first and second fluid compositions to be dispensed from the one or more dispensers into the catheter lumen, mixed by flowing the first and second fluid compositions through the catheter lumen, and dispensed from the fluid delivery port as a fluid mixture that reacts in situ to form the nonfluent closure composition adjacent the vessel puncture site;
- wherein the catheter is sized to block flow of the fluid mixture from the fluid delivery port into a substantial part of the tissue puncture, whereby a localized in situ closure forms adjacent the vessel puncture site to seal the vessel puncture site.

23. An assembly according to claim 22, further including a positioner on the distal end deformable to a collapsed condition for passage into the blood vessel and an enlarged condition engaging an interior wall of the blood vessel about the puncture site in response to application of outward tension on the catheter.

24. An assembly according to claim 22, wherein the positioner comprises a balloon structure expandable by fluid pressure.

25. An assembly according to claim 22, and further including a mixing chamber communicating with the catheter lumen.

26. An assembly according to claim 22, and further including a guidewire lumen in the catheter tube accommodating passage of a guidewire.

27. A method for sealing a vascular puncture site comprising the steps of introducing a catheter through a tissue puncture, the catheter including a distal end and at least one fluid delivery port adjacent the distal end to be positioned adjacent the vessel puncture site, the catheter being sized to occupy substantially all of the tissue puncture;

providing first and second fluid compositions which, upon mixing, react to form a nonfluent closure composition;

mixing the first and second fluid compositions by flowing the components through a lumen in the catheter that communicates with the fluid delivery port; and dispensing the first and second fluid compositions from the fluid delivery port as a fluid mixture that reacts in situ to form the nonfluent closure composition adjacent the vessel puncture site, the size of the catheter blocking flow of the fluid, mixture from the fluid delivery port into a substantial part of the tissue puncture, whereby a localized in situ closure forms adjacent the vessel puncture site to seal the vessel puncture site.

28. A method according to claim 27, further including the step of expanding a positioner carried on the distal end of the catheter tube inside the blood vessel, and applying outward tension upon the catheter tube to bring the expanded positioner against an interior wall of the blood vessel about the puncture site while the nozzle occupies a tissue region outside the puncture site.

29. A method according to claim 27 wherein the introducing step includes passing the catheter tube over a guidewire.

* * * * *

UNITED STATES PATENT AND TRADEMARK OFFICE
CERTIFICATE OF CORRECTION

PATENT NO. : 6,302,898 B1 Page 1 of 1
DATED : October 16, 2001
INVENTOR(S) : Stuart D. Edwards, Thomas Wehman, Theodore L. Parker, Eugene V. Skalnyi, Theodore Kucklick and John Evans It is certified that error appears in the above-identified patent and that said Letters Patent is hereby corrected as shown below:

<u>Title page,</u>
Item [73], Assignee should read -- Neo Mend, Inc. --.

Signed and Sealed this

Nineteenth Day of November, 2002

*Attest:*

JAMES E. ROGAN
*Attesting Officer* *Director of the United States Patent and Trademark Office*